United States Patent
Sarwal et al.

(10) Patent No.: US 12,188,949 B2
(45) Date of Patent: *Jan. 7, 2025

(54) NONINVASIVE METHOD TO QUANTIFY KIDNEY FUNCTION AND FUNCTIONAL DECLINE

(71) Applicant: The Regents of the University of California, Oakland, CA (US)

(72) Inventors: Minnie M. Sarwal, San Francisco, CA (US); Joshua Y. Yang, San Francisco, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,736

(22) Filed: Aug. 1, 2022

(65) Prior Publication Data

US 2023/0072969 A1    Mar. 9, 2023

Related U.S. Application Data

(63) Continuation of application No. 17/387,917, filed on Jul. 28, 2021, now Pat. No. 11,435,366, which is a continuation of application No. PCT/US2020/049387, filed on Sep. 4, 2020.

(60) Provisional application No. 62/896,296, filed on Sep. 5, 2019.

(51) Int. Cl.
| | | |
|---|---|---|
| *A61K 31/351* | (2006.01) | |
| *A61P 13/12* | (2006.01) | |
| *G01N 33/68* | (2006.01) | |
| *G01N 33/70* | (2006.01) | |

(52) U.S. Cl.
CPC .......... *G01N 33/6893* (2013.01); *A61P 13/12* (2018.01); *G01N 33/70* (2013.01); *G01N 2800/347* (2013.01)

(58) Field of Classification Search
CPC .......................... G01N 2800/00; A61K 31/351
USPC ............................................ 436/811; 514/23
See application file for complete search history.

(56) References Cited

U.S. PATENT DOCUMENTS

| | | |
|---|---|---|
| 9,970,927 B2 | 5/2018 | Yerramilli et al. |
| 11,435,366 B2 | 9/2022 | Sarwal et al. |
| 2010/0029013 A1 | 2/2010 | Lin et al. |
| 2012/0135886 A1 | 5/2012 | Ruddock et al. |
| 2013/0280172 A1 | 10/2013 | Xu et al. |
| 2016/0187348 A1 | 6/2016 | Yerramilli et al. |
| 2017/0166955 A1 | 6/2017 | Birnboim et al. |
| 2019/0120856 A1 | 4/2019 | Xie et al. |

FOREIGN PATENT DOCUMENTS

| | | |
|---|---|---|
| CN | 105988001 A | 10/2016 |
| WO | 2004046314 A2 | 6/2004 |

OTHER PUBLICATIONS

"Use of the IDEXX SDMA Test to Assess Kidney Function in Puppies and Kittens," SDMA Reference Interval Update, IDEXX, Aug. 2017, 2 pages.
Application No. PCT/US2020/049387, International Preliminary Report on Patentability, Mailed On Mar. 17, 2022, 9 pages.
Application No. PCT/US2020/049387, International Search Report and Written Opinion, Mailed On Jan. 21, 2021, 11 pages.
Raptis et al., "Role of Asymmetrical Dimethylarginine in the Progression of Renal Disease", Nephrology, vol. 18, No. 1, Jan. 2013, pp. 11-21.
Schulze et al., "Determination of Asymmetric Dimethylarginine (ADMA) Using a Novel ELISA Assay", Clinical Chemistry and Laboratory Medicine, vol. 42, No. 10, Feb. 2004, pp. 1377-1383.
Sitar, "Asymmetric Dimethylarginine and Its Relation as a Biomarker in Nephrologic Diseases", Biomark Insights, vol. 11, Dec. 7, 2016, pp. 131-137.
Tsikas et al., "Quantitative Determination of Circulating and Urinary Asymmetric Dimethylarginine (ADMA) in Humans by Gas Chromatography-tandem Mass Spectrometry as Methyl Ester Tri(N-Pentafluoropropionyl) Derivative", Journal of Chromatography B, vol. 798, No. 1, Dec. 5, 2003, pp. 87-99.
EP20860774.7, Extended European Search Report dated Jun. 19, 2023, 11 pages.
Eiselt et al., "Asymmetric Dimethylarginine and Progression of Chronic Kidney Disease—A One-Year Follow-Up Study," Kidney and Blood Pressure Research, vol. 39, No. 1, Jun. 3, 2014, pp. 50-57.

*Primary Examiner* — Raymond J Henley, III
(74) *Attorney, Agent, or Firm* — Kilpatrick Townsend & Stockton LLP

(57) ABSTRACT

Disclose are methods, compositions and kits for the determination of kidney function that provide an alternative to the standard-of-cure used for eGFR calculations. Described herein are methods for quantitative measurement of ADMA and hydration markers in a urine sample, and process used to transform the input of these methods into a measure of kidney function. The methods allow ADMA and other biomarkers to be detected in urine samples from a subject using a simple and inexpensive assay that can be easily performed noninvasively and only require urine samples for the prediction of kidney function.

27 Claims, 20 Drawing Sheets

NONINVASIVE METHOD TO QUANTIFY KIDNEY FUNCTION AND FUNCTIONAL DECLINE

CROSS-REFERENCES TO RELATED APPLICATIONS

The present application is a continuation of U.S. patent application Ser. No. 17/387,917 filed Jul. 28, 2021, which is a continuation of International Patent Application No. PCT/US2020/049387, filed Sep. 4, 2020, which claims priority to U.S. Provisional Patent Application No. 62/896,296, filed on Sep. 5, 2019, which are incorporated herein by reference in their entirety for all purposes.

BACKGROUND

Fourteen percent of the United States population is afflicted with chronic kidney disease (CKD). Approximately 661,000 Americans have renal failure, of which, approximately 468,000 are on dialysis. The high incidence of CKD contributes to health care costs of approximately $80,000 US dollars, per patient, per year. Further, approximately 193,000 Americans have a functioning kidney transplant and 30,000 patients receive new kidney transplants every year—incurring health care costs of approximately $100,000-$200,000 US dollars yearly for each transplant, and $20,000 US dollars, per patient, per year for immunosuppression. In 2015, Medicare alone spent 64 Billion USD for treatment of chronic kidney disease alone (11% of total covered patients).

Accurate assessment of renal function is imperative to allow for proper tracking of kidney function or injury. In the case of renal transplantation, renal dysfunction can be associated with 15%— 30% of cases that require treatment with augmented immunosuppression. Usually, 130,000 transplants are rejected after the first 10 years of graft transplantation, making it very important to have accurate and non-invasive tests for kidney function or kidney injury. Nonetheless, the current standard of care does not allow for proper distinction between various underlying causes of either kidney function or injury, such as acute insult/recovery, chronic damage/progression of injury, time assessment for renal replacement therapy, or assessment of dialysis/transplantation needs.

Consider for instance the severe limitations of a widely used test for measuring renal function, namely the serum creatinine (SCr) blood test. First, the SCr test is a blood test, and the requirement for a blood draw limits its utility in a non-invasive manner. Second, serum creatinine is a late marker of advanced kidney injury and is not specific for the diagnosis of acute rejection (AR). In fact, SCr blood test is confounded by multiple variables as serum creatinine can rise with multiple causes unrelated to kidney function, such as volume depletion, infection, and obstruction. Furthermore, SCr measurements are further confounded by variables such as gender, hydration status, diet and muscle mass. As a result, while the cost of a SCr test is low, the lack of specificity of the SCr test and the influence of confounding variables limit the clinical utility of the test.

Additionally, the current standard of care for measuring kidney function—the glomerular filtration rate (GFR; also referred to as estimated glomerular filtration rate eGFR)—is perhaps even more limited than the SCr test. In chronic kidney disease, the kidneys lose their ability to effectively filter waste products in the blood because of damage to the glomeruli of nephrons. The standard glomerular filtration rate tests evaluate some level of kidney function by measuring the volume of plasma that the kidneys filter through the glomeruli per unit time. However, there are numerous limitations with the current eGFR tests. First, eGFR requires a blood sample and thus cannot readily be used in a non-invasive setting. Second, eGFR measurements are limited by demographic data collection. eGFR tests provide a measure of how well the kidneys are removing wastes and excess fluid from the blood by inputting a detected serum creatinine level in an equation, along with parameters for age and gender adjustments, and in some instances additional adjustments for those of African American descent. However, there is a lack of a consensus about what formula should be used to estimate glomerular function, where some prefer the Modification of Diet in Renal Disease (MDRD) equation and others the Cockcroft-Gault (CG) equation, as some believe the MDRD equation significantly underestimates the measured GFR when compared with the CG formula. Recently, calculation of the eGFR is done by the chronic kidney disease epidemiology collaboration formula (CKD-EPI).

Lastly, more sensitive measurements of eGFR are available through the use of inulin, a molecule that is not endogenous in humans. When inulin is used to measure eGFR, a specified mass comprising inulin is injected into a person's bloodstream and the amount of inulin cleared through the urine is indicative of the amount of plasma filtered by the body's glomeruli. Unfortunately, inulin eGFR not only requires a blood draw, but it also typically requires a patient to stay in an outpatient setting, further limiting its utility. Moreover, the inulin GFR test is quite costly relative to SCr or non-inulin eGFR tests, making this test something that is rarely used in an actual clinical setting.

There currently do not exist any urine-based methods for eGFR prediction or estimation of kidney function. Current methods for kidney function assessment largely consist of semi-quantitative measures of leukocytes, nitrite, urobilinogen, protein, pH, blood, specific gravity, ketone, bilirubin, and glucose. These tests merely identify the presence of late-stage kidney disease and functional decline and do not provide a quantitative estimate of kidney function.

BRIEF SUMMARY

Provided herein are methods for determining kidney function that quantify the presence of biomarkers in urine and transform the input of these biomarkers to estimate the glomerular filtration rate (GFR) of a subject.

In one aspect, provided are methods for determining kidney function in a subject, the method comprising: contacting a urine sample from the subject with a coupling agent; detecting the amount of asymmetric dimethylarginine (ADMA), or symmetrical dimethylarginine (SDMA), or both ADMA and SDMA in the sample; and determining kidney function in the subject based on the amount of ADMA, SDMA, or both ADMA and SDMA in the sample. In some aspects, the detection of ADMA and SDMA is combined with the detection of other markers in a lateral flow assay (LFA) test.

In some embodiments, the coupling agent is selected from N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); or (2,5-dioxopyrrolidin-1-yl) prop-2-enyl carbonate.

In some aspects provided herein is method comprising: (a) contacting a urine sample with an antibody that specifically binds to asymmetric dimethylarginine (ADMA); and (b) detecting an amount of the antibody that is in a bound state; (c) determining an amount of ADMA from the urine sample based on the amount of the antibody that is in the bound state; and (c) either contacting the urine sample with a probe to determine an amount of a urinary biomarker that is indicative of the subject's hydration level; or determining a urine specific gravity of the urine sample. In some cases, the antibody that specifically binds ADMA has a reactivity for symmetric dimethylarginine (SDMA) that is less than 25%, less than 10%, less than 5%, or less than 1% of its reactivity for ADMA. In some cases, the method further comprises contacting the urine sample with the probe to determine an amount of the urinary biomarker that is indicative of the subject's hydration level, and the urinary biomarker that is indicative of the subject's hydration level may be urine SDMA or urine creatinine. In some embodiments, the probe that is specific to SDMA is an antibody that has a reactivity for ADMA that is less than 25%, less than 10%, less than 5%, or less than 1% of its reactivity for SDMA. In some cases, the method further comprises determining the urine specific gravity of the urine sample. In some aspects, the method further comprises determining the specific gravity of the urine sample. In some aspects, the method further comprises contacting the urine sample with a reagent that reacts with free ADMA to form an ADMA conjugate prior to contacting the urine sample with the antibody that specifically binds to ADMA. ADMA may be bound to the antibody as either free ADMA or the conjugate that results after the aforementioned coupling. The reagents may be selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In some instances, the amount of ADMA is determined via an enzyme-linked immunosorbent assay (ELISA), such as a competitive ELISA. In some instances, the amount of ADMA is determined via a lateral flow assay. In some instances, the urine sample is a diluted urine sample. In some instances, the method further comprises detecting an amount of at least one, at least two, at least three, at least four, or at least five biomarkers in the urine sample, wherein the biomarkers are selected from creatinine, total protein, 5-methylcytosine, cell-free DNA, methylated cell-free DNA, CXCL10, and clusterin. In some cases the subject is a mammal, such as human, a domesticated cat or a dog. In some instances, the method further comprises administering a treatment to the subject, including, but not limited to administering a diabetic kidney disease-targeted drug, a SGLT-2 receptor inhibitor, a SIRT1 agonist, or a bromodomain inhibitor to the subject if the subject is diagnosed with diabetic kidney disease. In other cases the treatment comprises administering a steroid therapy to the subject if the subject is diagnosed with IgA/Non-IgA mesangial proliferative glomerulonephritis or membrano-proliferative glomerulonephritis. In some instances, the treatment comprises dialysis.

In some aspects provided herein is a method for determining kidney function of a subject from a urine sample, the method comprising: detecting an amount of asymmetric dimethylarginine (ADMA) from a urine sample of a subject; assaying the urine sample to determine a hydration status of the subject; and generating a value indicative of the kidney function of the subject based on the amount of ADMA from the urine sample and the hydration status of the subject; determining the kidney function of subject based on the value.

In some instances, generating a value indicative of the kidney function of the subject comprises inputting the amount of ADMA and the hydration status of the subject into an algorithm to produce the value. In such instances, the algorithm may be implemented via a computer system. In some instances, determining the kidney function of the subject comprises comparing the value to a threshold and determining the kidney function of the subject based on the comparison. In some instances, generating the value indicative of the kidney function of the subject comprises inputting a determined amount of a hydration marker from the urine sample into the algorithm to produce the value, the hydration marker can be creatinine, SDMA, or both. In some instances, generating the value indicative of the kidney function of the subject comprises inputting a specific gravity of the urine sample into the algorithm to produce the value, inputting an amount of total protein from the sample into the algorithm, inputting an age of the subject into the algorithm, or inputting a gender of the subject into the algorithm. In some instances, a race of the subject is not input into the algorithm. In some cases, the amount of urine ADMA from the urine sample of the subject positively correlates with glomerular filtration rate (GFR). In some instances, the value indicative of the kidney function of the subject is an estimated GFR. In some instances, the hydration status of the subject is an amount of a urinary marker that is indicative of a hydration level in the subject, and the hydration mark can be urine SDMA or urine creatinine. In some instances, assaying the urine sample to determine the hydration status of the subject comprises determining a urine specific gravity of the urine sample. In some cases, the hydration status of the subject is represented by the specific gravity of the urine sample. In some cases, the method further comprises coupling a reagent to ADMA prior to detecting the amount of ADMA from the urine sample, and the reagent can be selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In some cases, the step of detecting the amount of ADMA from the urine sample of the subject comprises: contacting the urine sample with an antibody that specifically binds to ADMA; and detecting an amount of the antibody that is in a bound state. In some aspects, the antibody that specifically binds ADMA has a reactivity for symmetric dimethylarginine (SDMA) that is less than 25%, less than 10%, less than 5%, or less than 1% of its reactivity for ADMA. In some aspects, the subject is identified as having impaired kidney function when the ADMA is in the urine sample at a concentration of less than 19.4 µM. In some instances, the subject is identified as having impaired kidney function when the ADMA/creatinine ratio or ADMA/SDMA ratio is less than 0.3 µM/mg/dL or 0.7 µM/mg/dL, respectively. In some aspects, the method further comprises (1) identifying the subject as having impaired kidney function and (2) administering a treatment to the subject based on the identified impairment of kidney function.

In some aspects, provided herein is a method for detecting kidney injury in a subject, the method comprising: determining the kidney function of the subject according to the methods described above; and detecting amounts of two or more biomarkers in the urine sample of the subject, wherein the two or more biomarkers are selected from the group consisting of creatinine, total protein, 5-methyclytosine, cell-free DNA, methylated cell-free DNA, CXCL10, and clusterin. In some aspects, the method further comprises administering a treatment to the subject if the subject has decreased kidney function indicative of kidney disease or kidney injury. The treatment may comprise administering a diabetic kidney disease-targeted drug, a SGLT-2 receptor inhibitor, a SIRT1 agonist, or a bromodomain inhibitor to the subject if the subject is diagnosed with diabetic kidney disease, a steroid therapy to the subject if the subject is diagnosed with IgA/Non-IgA mesangial proliferative glomerulonephritis or membrano-proliferative glomerulonephritis. The IGA nephropathy may be identified with a sensitivity of at least 95% and a specificity of at least 98%. In some instances, the treatment comprises dialysis.

In another aspect, a kit is provided, the kit comprising: (i) reagents for detecting ADMA, SDMA, or both ADMA and SDMA in a urine sample; and (ii) a coupling agent. In some embodiments, the coupling agent is selected from N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); or (2,5-dioxopyrrolidin-1-yl) prop-2-enyl carbonate.

In some aspects, the disclosure provides a kit for use in detecting kidney function in a subject, the kit comprising: an antibody for detecting ADMA; a reagent for covalent conjugation to ADMA; and a reagent for assessing hydration status of the subject. In some aspects, the kit further comprises a detection reagent for detecting total urinary protein. In some aspects, the antibody for detecting ADMA has a reactivity for symmetric dimethylarginine (SDMA) that is less than 25%, less than 10%, less than 5%, or less than 1% of its reactivity for ADMA. In some aspects, the reagent for covalent conjugation to ADMA is selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In other cases, the kit further comprises a reagent for binding to cell-free DNA, a reagent for binding to CXCL10, a reagent for binding to creatinine, a reagent for binding to 5-methyclytosine, a reagent for binding to methylated cell-free DNA, a reagent for binding to clusterin, or a combination of two of more of the aforementioned reagents. In some instances, the kit comprises a receptacle for containing a urine sample and a lateral flow device.

In some aspects, the disclosure provides a reaction mixture comprising: a urine sample of a subject, a reagent for covalent conjugation to ADMA, and an antibody to ADMA. In some instances, the reagent for covalent conjugation to ADMA is selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In some instances, the antibody to ADMA has a reactivity for symmetric dimethylarginine (SDMA) that is less than 25%, less than 10%, less than 5%, or less than 1% of its reactivity for ADMA. In some cases the subject is a mammal, such as a human, a domesticated cat or a dog. The coupling agent may be selected from N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); or (2,5-dioxopyrrolidin-1-yl) prop-2-enyl carbonate.

In another aspect, provided is a reaction mixture comprising a urine sample, a coupling agent, and antibodies that specifically bind ADMA, SDMA, or both ADMA and SDMA. In some embodiments, the coupling agent is selected from N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); or (2,5-dioxopyrrolidin-1-yl) prop-2-enyl carbonate.

In another aspect, a method of treating a disease associated with decreased kidney function in a subject is described, the method comprising the steps of: (a) selecting a subject having decreased kidney function as determined by (i) an ADMA concentration less than 19.421 μM; or (ii) an ADMA/creatinine ratio less than 0.312 (μM/mg/dL); or (iii) an ADMA/SDMA ratio less than 0.694; or (iv) an eGFR less than 90 mL/min per 1.73 m$^2$; or (v) a $KIT_{GFR}$ less than 90 mL/min per 1.73 m$^2$; and (b) administering a treatment to the subject.

BRIEF DESCRIPTION OF THE DRAWINGS

FIG. 5A. An IgA Risk Score ranging from 0 to 100 segregated healthy control patients from those with IgA nephropathy. Urine samples were collected from healthy controls (n=64) who had no evidence of kidney disease or injury as assessed by both absence of proteinuria and eGFR greater than 120 mL/min per 1.73 m². All urine samples from IgA patients (n=67) were used, as none of these patients had remission of IgA during the treatment duration. FIG. 5B. Receiver-operator characteristic (ROC) curves of the IgA Risk Score with AUC of 0.994 (P<0.0001) and proteinuria. For the IgA Risk Score, at a threshold of 57.4, the sensitivity and specificity were 95.5% and 98.4% respectively. **** P<0.0001.

DEFINITIONS

Figure 1A:
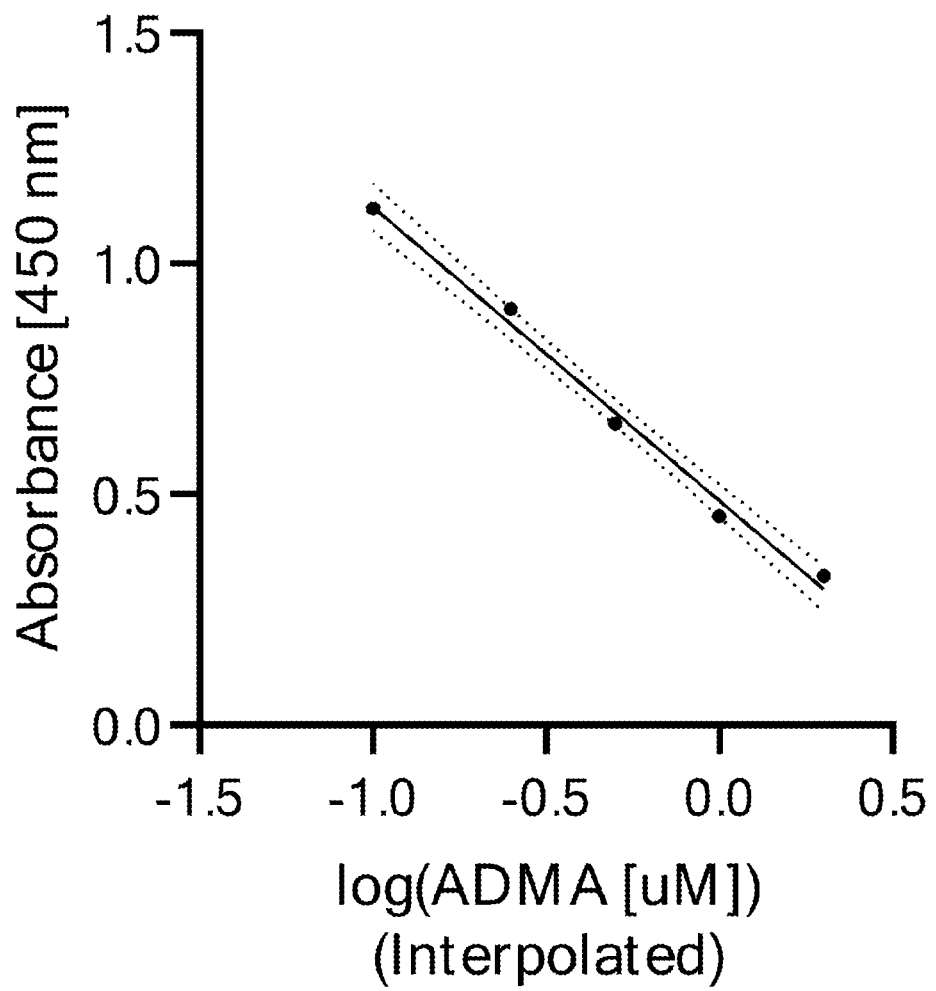
FIG. 1A shows an example fit for ADMA using the analysis methods described herein.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "biofluid" or "biofluidic sample" refers to a fluidic composition that is obtained or derived from an individual that is to be characterized and/or identified, for example based on physical, biochemical, chemical and/or physiological characteristics. Non-limiting examples of biofluid include blood, serum, plasma, saliva, phlegm, gastric juices, semen, tears, and sweat. In one embodiment the biofluid is urine.

As used herein, the term "AUC" refers to "area under the curve" or C-statistic, which is examined within the scope of ROC (receiver-operating characteristic) curve analysis. AUC is an indicator that allows representation of the sensitivity and specificity of a test, assay, or method over the entire range of test (or assay) cut points with just a single value. An AUC of an assay is determined from a diagram in which the sensitivity of the assay on the ordinate is plotted against 1-specificity on the abscissa. A higher AUC indicates a higher accuracy of the test; an AUC value of 1 means that all samples have been assigned correctly (specificity and sensitivity of 1), an AUC value of 50% means that the samples have been assigned with guesswork probability and the parameter thus has no significance.

Using AUCs through the ROC curve analysis to evaluate the accuracy of a diagnostic or prognostic test are well known in the art, for example, as described in, Pepe et al., "Limitations of the Odds Ratio in Gauging the Performance of a Diagnostic, Prognostic, or Screening Marker," Am. J. Epidemiol 2004, 159 (9): 882-890, and "ROC Curve Analysis: An Example Showing The Relationships Among Serum Lipid And Apolipoprotein levels In Identifying Subjects With Coronary Artery Disease," Clin. Chem., 1992, 38(8): 1425-1428. See also, CLSI Document EP24-A2: Assessment of the Diagnostic Accuracy of Laboratory Tests Using Receiver Operating Characteristic Curves; Approved Guideline—Second Edition. Clinical and Laboratory Standards Institute; 2011; CLSI Document I/LA21-A2: Clinical Evaluation of Immunoassays; Approved Guideline—Second Edition. Clinical and Laboratory Standards Institute; 2008.

As used herein, the term "diagnose" means assigning symptoms or phenomena to a disease or injury. For the purpose of this invention, diagnosis means determining the presence of organ injury in a subject.

As used herein, the term "predict" refers to predicting as to whether organ injury is likely to develop in a subject.

As used herein, the terms "glomerular filtration rate" ("GFR"), "estimated glomerular filtration rate" ("eGFR"), and "actual glomerular filtration rate" ("actual GFR"), refer to a measure of kidney function that uses a person's age, gender, and blood creatinine level.

As used herein, the terms "$KIT_{Function}$", "$KIT_{GFR}$", is a measurement of kidney function that incorporates measurements of SDMA, ADMA, urine creatinine, urine protein, and age of patient as inputs into a suitable formula, such as the formula below.

$$eGFR = SDMA + \frac{277 + 140 \times ADMA}{Gender_F + SDMA} +$$

$$83.321 * \min(greaterorequal)(37 \times ADMA, \text{Protein}),$$

$$SDMA^2 \times \frac{\min(0.288, \text{Citrate})}{Age \times ADMA}\Big) - \min(\text{Protein},$$

$$\min(48.065 + ADMA, \text{Creatinine}))$$

Alternative suitable formulas are further described in the specifications.

As used herein, a urinary biomarker that is indicative of the subject's hydration level, or a "hydration marker", or "a marker of hydration status", refers to creatinine and SDMA, either used jointly or individually.

As used herein, the abbreviation SDMA refers to symmetric dimethylarginine.

As used herein, the abbreviation ADMA refers to asymmetric dimethylarginine.

As used herein, the abbreviation "KIT biomarkers" refers to a composite of six biomarkers, namely cell-free DNA (cfDNA), methylated cfDNA, clusterin, creatinine, protein, and CXCL10 biomarkers used in kidney injury test (KIT) assay urinary biomarkers to detect kidney injury.

As used herein, the term "probe" refers to an agent that binds to a biomarker in urine. The term "probe" includes antibodies that bind to biomarkers, including biomarkers that indicate a subject's hydration level.

As used herein, and as generally used in the art, "urine specific gravity" (USG) is a measure of the concentration of particles in urine and the density of urine compared with the density of water.

DETAILED DESCRIPTION

Figure 7:
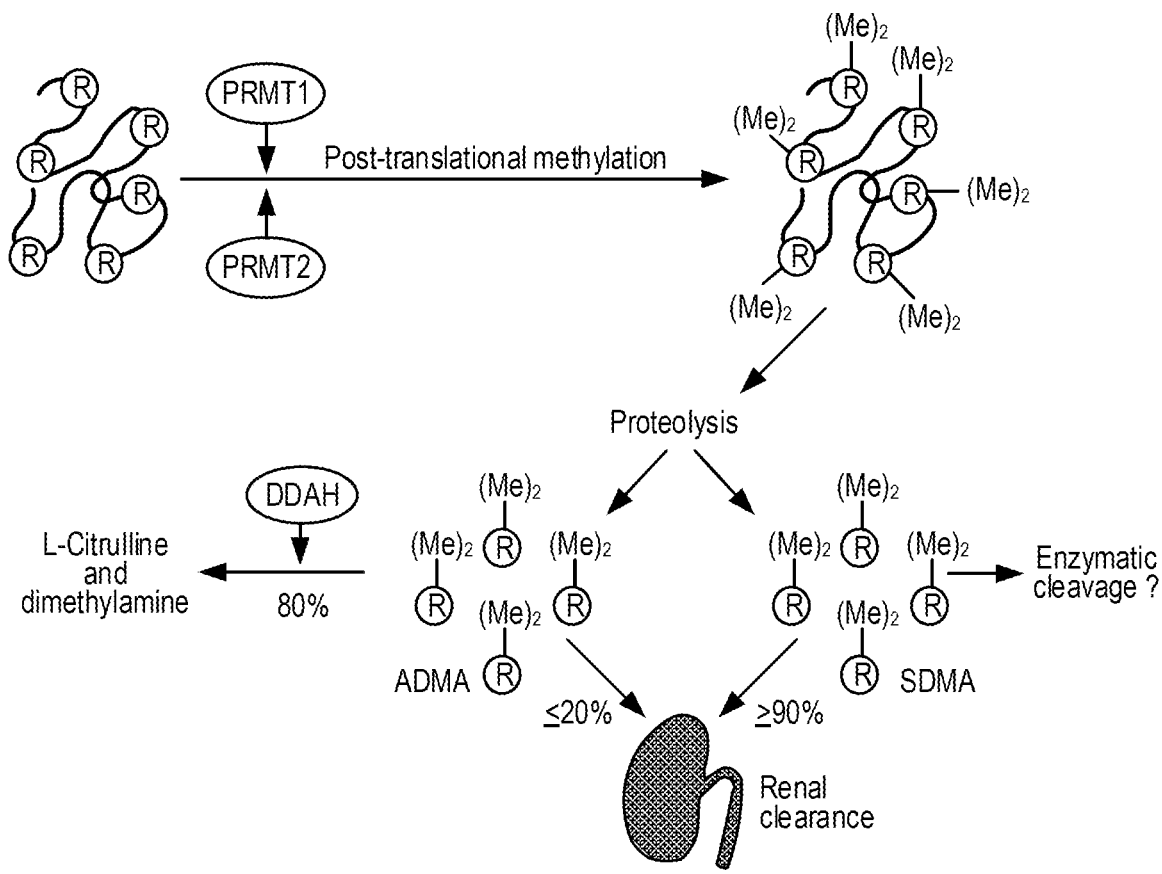
FIG. 7 is a schematic illustrating that SDMA is renally cleared regardless of the degree of kidney functional impairment, in contrast ADMA is degraded.

The present disclosure provides methods, compositions and kits for the quantitative measurement of SDMA and ADMA in a urine sample. Asymmetric dimethylarginine (ADMA) is an endogenous inhibitor of NO-synthase. It is formed during proteolysis of methylated proteins and removed by renal excretion or metabolic degradation by the enzyme dimethylarginine dimethylaminohydrolase (DDAH). Several cell types, including human endothelial and tubular cells are capable of synthesizing and metabolizing ADMA. The disclosure demonstrates that SDMA and ADMA can be detected in urine samples from a subject using a simple and inexpensive assay which can be easily performed in most clinical laboratories. Notably, the instant disclosure demonstrates that urinary ADMA is both positively and strongly correlated with kidney function, and thus can be used as a biomarker for kidney function, an unexpected result in view of the characterization in the art of serum ADMA as being negatively and weakly correlated with GFR. Consider for example, that SDMA is almost entirely renally cleared (see FIG. 7). Meanwhile, the majority of ADMA is instead degraded. When the kidney is injured the enzymes that degrade ADMA may be upregulated, providing different patterns of ADMA and SDMA for kidney function and injury.

The methods described herein provide the following advantages. The methods are fully noninvasive and only require urine samples for the prediction of kidney function. No blood draws are required and thus skilled technicians/phlebotomists are not required. Minimal sample processing is required prior to quantification, as the metabolic biomarkers of interest do not degrade rapidly, or they are amenable to being treated with a stabilizing solution.

In one aspect, the method comprises a microwell assay format and analysis methods that integrates the SDMA and ADMA biomarkers, additional biomarkers, and clinical/demographic parameters of the subject to provide a functional kidney score and/or predicted eGFR measurement. In one aspect, the method is a urinary ELISA assay for detecting dimethylarginine (ADMA) and symmetrical dimethylarginine (SDMA) in a urine sample from a subject. In some embodiments, the method is a competitive enzyme-linked immunoassay. In some aspects, the method comprises (a) contacting a urine sample with an antibody that specifically binds to asymmetric dimethylarginine (ADMA); and (b) detecting an amount of the antibody that is in a bound state; (c) determining an amount of ADMA from the urine sample based on the amount of the antibody that is in the bound state; and (c) either contacting the urine sample with a probe to determine an amount of a urinary biomarker that is indicative of the subject's hydration level; or determining a urine specific gravity of the urine sample. In some instances, the urine sample is contacted with a reagent that reacts with free ADMA to form an ADMA conjugate prior to contacting the urine sample with the antibody that specifically binds to ADMA. The ADMA that is bound to the antibody can be either free ADMA or the conjugate that results after coupling.

In some embodiments, urinary ADMA and SDMA are derivatized by contacting the urine sample with a coupling agent. In some embodiments, the coupling agent is a compound that comprises an NHS ester moiety. In some embodiments, the compound is based on amine-reactive crosslinker chemistry whereby primary amines (—NH$_2$) are reacted with various chemical groups that enable subsequent conjugation of other chemicals of interest and typically conjugate based on acylation or alkylation. The conjugation chemistry is described below:

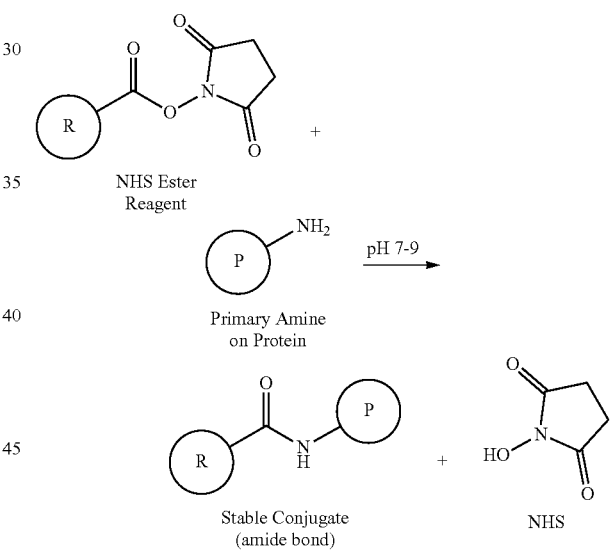

In some embodiments, the coupling agent is selected from the group consisting of N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); and (2,5-dioxopyrrolidin-1-yl) prop-2-enyl carbonate.

The coupling agent provides the following advantages. First, without being bound by theory, ADMA and SDMA are small molecules, and antibodies may bind to the derivatized ADMA with higher affinity than the non-derivatized ADMA because this class of antibodies are generated against ADMA conjugated to either KLH or BSA. As such, while the antibody binds ADMA, it actually has higher binding affinity for a region consisting of ADMA and the derivatization linker. Furthermore, ADMA and SDMA can occur internally within a protein sequence, as they are derivatives of arginine, a common amino acid. By using a derivatization agent, the likelihood of cross-reactivity towards internal ADMA/SDMA moieties (i.e., within a protein sequence) versus free ADMA/SDMA is reduced as the antibodies can bind to the derivatization linker in addition to the ADMA/SDMA molecule in the free-form, but cannot bind ADMA/SDMA within the amino acid sequence of a protein as the derivatization agent does not chemically react with internal ADMA/SDMA. The urinary biomarker that is indicative of the subject's hydration level can be selected from the group consisting of urine SDMA and urine creatinine and it may be detected with suitable methods described in the art, including ELISA. In some instances, the antibody that specifically binds ADMA has a reactivity for symmetric dimethylarginine (SDMA) that is less than 50%, less than 45%, less than 40%, less than 35%, less than 30%, less than 25%, less than 20%, less than 15%, less than 10%, less than 5%, or less than 1% of its reactivity for ADMA. In some instances, the antibody that specifically binds SDMA has a reactivity for asymmetric dimethylarginine (ADMA) that is less than 50%, less than 45%, less than 40%, less than 35%, less than 30%, less than 25%, less than 20%, less than 15%, less than 10%, less than 5%, or less than 1% of its reactivity for SDMA.

Second, while it is possible to create competitive immunoassays that do not use a derivatization agent (e.g. by direct conjugation of the small molecule to the adsorbent component, such as BSA), this creates significant steric hindrance that reduces the ability of the antibody to bind the molecule of interest, thus reducing overall affinity. Thus, derivatization allows detecting the small molecules ADMA and SDMA in a competitive immunoassays with high sensitivity.

In some embodiments, ELISA wells are coated with ADMA or SDMA, and an antibody against ADMA or SDMA is mixed with the diluted urine sample of interest and is added to these wells. The endogenous ADMA or SDMA in the sample that has been derivatized competes with the well-bound ADMA or SDMA for antibody binding. In some embodiments, the sample is washed, and antibody binding is detected using a detectable label. In some embodiments, the detectable label is a peroxidase-conjugated antibody that can added to each microtiter well to detect the anti-ADMA or anti-SDMA antibodies. In some embodiments, the detectable label is detected contacting the sample with tetramethylbenzidine (TMB) or a chemiluminescent substrate solution such as SuperSignal FEMTO ELISA (Thermo Fisher), which is a substrate for peroxidase. In embodiments where the substrate is TMB, the enzymatic reaction can be terminated by an acidic stop solution. In some embodiments, the absorbance is measured by a spectrophotometer at 450 nm or the luminescence by a luminometer. In a competitive enzyme-linked immunoassay, the intensity of the signal is inversely proportional to the ADMA or SDMA concentration in the urine sample, as a high ADMA or SDMA concentration in the sample reduces the urine specific gravity of well-bound antibodies and lowers the signal.

In some instances, a lateral flow assay LFA dipstick is configured for the detection ADMA, SDMA, creatinine or both. These markers are indicative of various different kidney failure modes. The results of the test may be read using a benchtop lateral flow assay reader such as the Qiagen LR3, Axxin readers, or another suitable reader. The output of these tests may be plugged into an injury test of the disclosure.

In some embodiments, the urine sample is diluted to ensure that interference from other urinary components do not interfere with the assay and to ensure that the concentration of ADMA or SDMA falls within the linear and/or quantifiable range of the assay. Dilution of the urine sample can be done with 1× PBS, bovine serum albumin (BSA) in 1×PBS (where the concentration can range from 1% to 5%), or human serum albumin (HSA) in the range of 3.5 to 5.5 g/dL in 1×PBS.

Figure 1B:
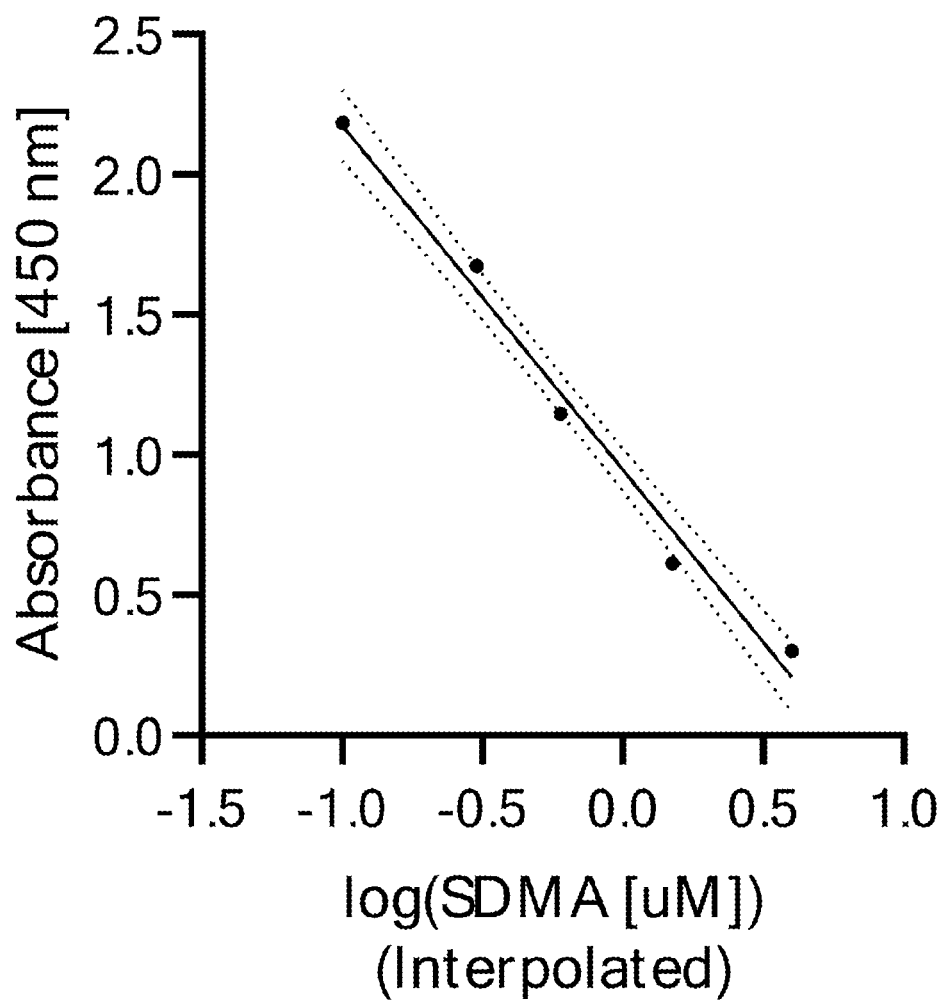
FIG. 1B shows an example fit for SDMA using the analysis methods described herein.

In some embodiments, unknown samples are interpolated to the values from a known standard of ADMA or SDMA values via curve-fitting such as that done by a 4-parameter or 5-parameter logistic, or a log-linear fit. An example fit for ADMA is shown in FIG. 1A. An example fit for SDMA is shown in FIG. 1B. The fits from these curves can be used to create a score for the quantitation of kidney function based on ADMA/SDMA measurements. In some instances, generating the value indicative of the kidney function of the subject comprises inputting an age and a gender of the subject into the algorithm, but do not require an input of the race of a subject.

A non-limiting example of how ADMA/SDMA measurements can be computed and transformed into a score that is representative of kidney function is as follows:

$$eGFR = SDMA + \frac{277 + 140 \times ADMA}{Gender_F + SDMA} +$$

$$83.321 * \min(greaterorequal)(37 \times ADMA, \text{Protein}),$$

$$SDMA^2 \times \frac{\min(0.288, \text{Citrate})}{\text{Age} \times ADMA}\Bigg) -$$

$$\min(\text{Protein}, \min(48.065 + ADMA, \text{Creatinine})).$$

In some aspects, the sensitivity of the test can be increased by detecting an amount of at least one, at least two, at least three, at least four, or at least five biomarkers in the urine sample, wherein the biomarkers are selected from creatinine, total protein, 5-methylcytosine, cell-free DNA, methylated cell-free DNA, CXCL10, and clusterin.

Data Analytics

Figure 2A:
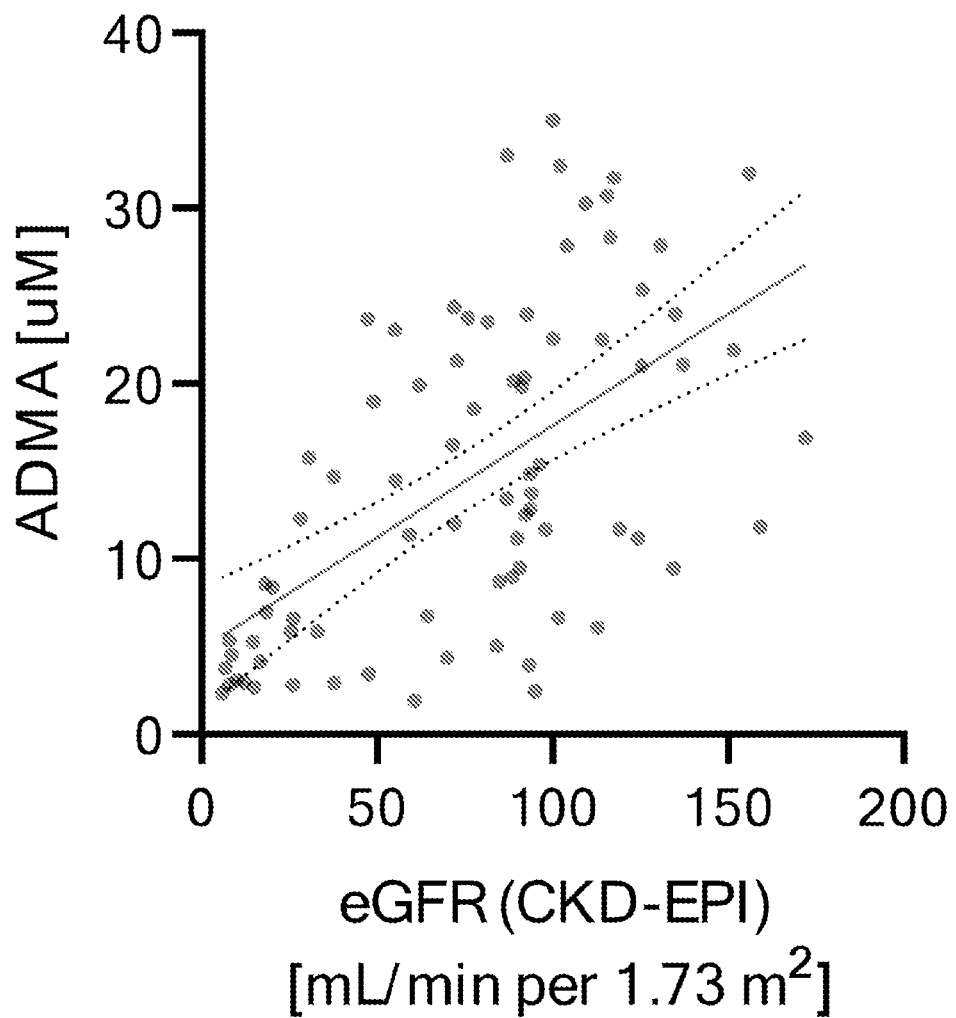
FIG. 2A shows that the kidney health of an individual can be determined by comparing the quantity of ADMA in the urine sample to a cutoff value indicative of kidney injury status, which may be a pre-determined clinical threshold or relative to a patient's baseline ADMA value.

In some embodiments, the method is used to determine kidney function or kidney health in a subject. In some embodiments, determination of kidney health of an individual comprises comparing the quantity of ADMA in the urine sample to a cutoff value indicative of kidney injury status, which can be a pre-determined clinical threshold or is relative to a patient's baseline ADMA value (See FIG. 2A).

In some instances, a cut off value that is indicative of kidney injury status can be an ADMA value less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, or less than 5 μM. In some embodiments, an ADMA value less than 19.421 μM indicates the subject has reduced kidney function or kidney disease.

In some embodiments, kidney health or kidney function is determined by a ratio of ADMA to a biomarker of a subject's hydration level. In some embodiments, the biomarker of the subject's hydration level is creatinine, and kidney health or kidney function is determined by the ADMA/creatinine ratio. In some instances, an ADMA/creatinine ratio that is indicative of kidney injury status is a ratio of less than 2.0 (μM/mg/dL), less than 1.9 (μM/mg/dL), less than 1.8 (μM/mg/dL), less than 1.7 (μM/mg/dL), less than 1.6 (μM/mg/dL), less than 1.5 (μM/mg/dL), less than 1.4 (μM/mg/dL), less than 1.3 (μM/mg/dL), less than 1.2 (μM/mg/dL), less than 1.1 (μM/mg/dL), less than 1.0 (μM/mg/dL), less than 0.9 (μM/mg/dL), less than 0.8 (μM/mg/dL), less than 0.7 (μM/mg/dL), less than 0.6 (μM/mg/dL), less than 0.5 (μM/mg/dL), less than 0.4 (μM/mg/dL), less than 0.3 (μM/mg/dL), less than 0.2 (μM/mg/dL), or less than 0.1 (μM/mg/dL). In some embodiments, an ADMA/creatinine ratio of less than 0.312 (μM/mg/dL) indicates the subject has reduced kidney function or kidney disease.

Figure 2B:
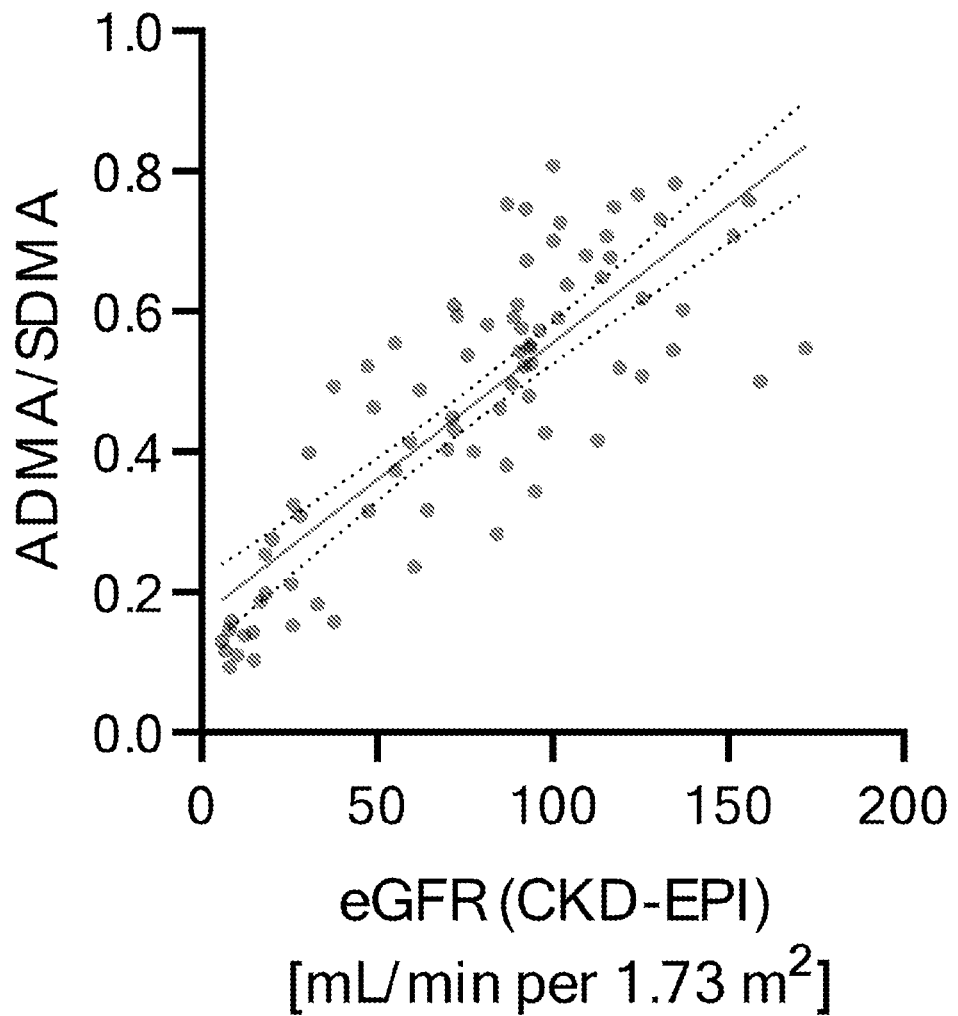
FIG. 2B shows that the kidney health of an individual can be determined by comparing the ratio of the ADMA/SDMA in the urine sample to a cutoff value indicative of kidney injury status, which may be a pre-determined clinical threshold or relative to a patient's baseline ADMA/SDMA ratio value.
Figure 2C:
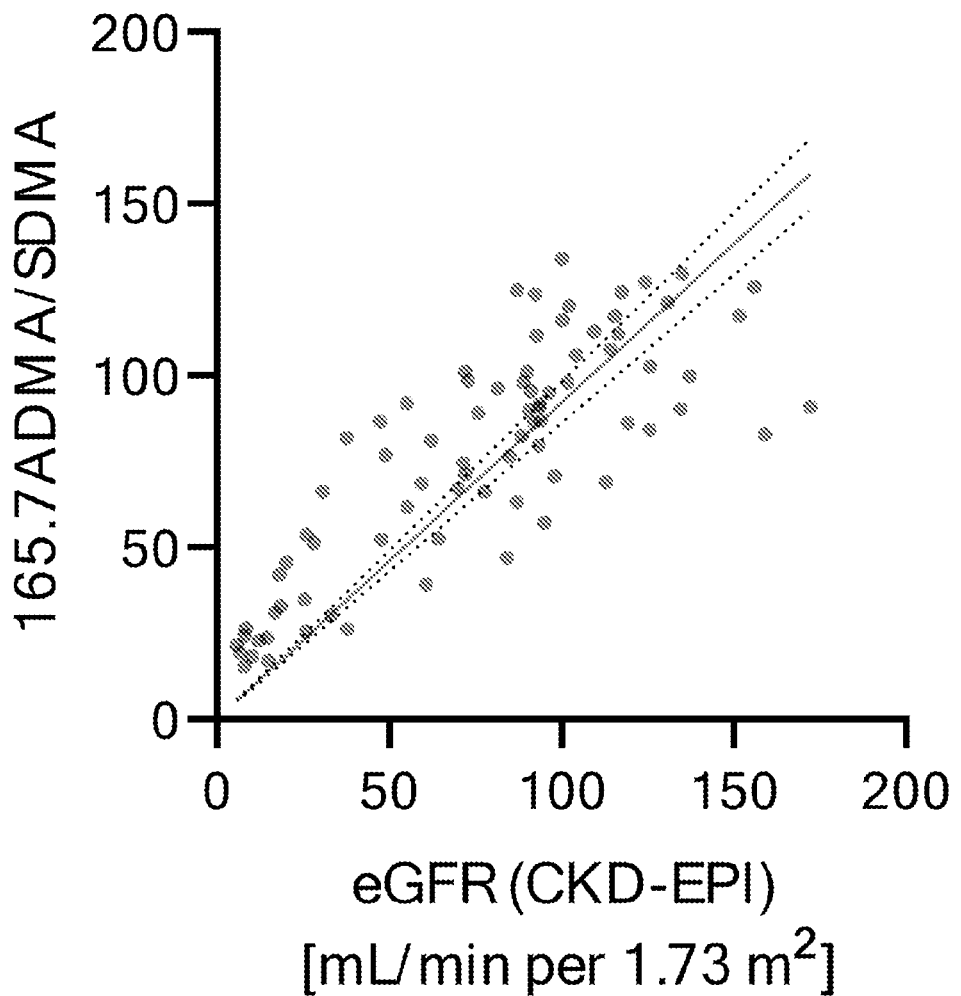
FIG. 2C shows that the ratio of ADMA/SDMA in the urine sample can be used to calculate an approximation of a known clinical parameter, the estimated glomerular filtration rate (eGFR).
Figure 2D:
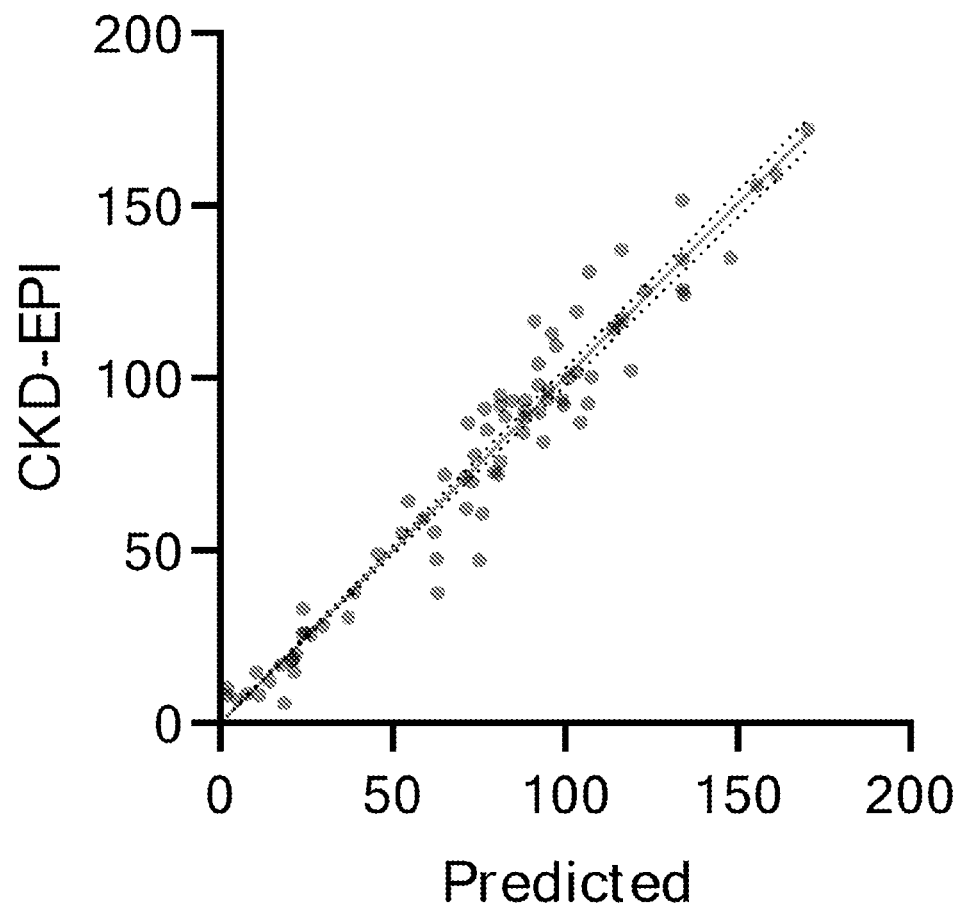
FIG. 2D shows that a representative functional score can be used to determine CKD in a subject.

In some embodiments, the determination of kidney health of an individual comprises comparing the ratio of the ADMA/SDMA in the urine sample to a cutoff value indicative of kidney injury status, which may be a pre-determined clinical threshold or relative to a patient's baseline ADMA/SDMA ratio value (FIG. 2B) This ratio may be multiplied by a constant in the form of c*ADMA/SDMA. In a specific case, the value of c is 165.7 when ADMA and SDMA are measured in micromolar [μM]. This particular form enables the calculation to approximate a known clinical parameter, the estimated glomerular filtration rate (eGFR) (FIG. 2C). In some instances, an ADMA/SDMA ratio that is indicative of kidney injury status is a ratio of less than 5.0, less than 4.9, less than 4.8, less than 4.7, less than 4.6, less than 4.5, less than 4.4, less than 4.3, less than 4.2, less than 4.1, less than 4.0, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, or less than less than 0.1. In some embodiments, an ADMA/SDMA ratio less than 0.694 indicates the subject has reduced kidney function or kidney disease.

In some embodiments, a functional score is used to determine kidney function in a subject. In some embodiments, the functional score is estimated GFR (eGFR). In some embodiments, the functional score is a composite value that is calculated based on the quantity of ADMA and SDMA detected in the urine samples. The functional score can be, for example, calculated from the mathematical relationships described in FIGS. 1-3, along with the input of other relevant data, such as age and gender. In some embodiments, additional biomarkers, such as citrate, can be used to calculate the composite value. In some embodiments, additional biomarkers present in the urine sample, including but not limited to creatinine, total protein, 5-methylcytosine, cell-free DNA, methylated cell-free DNA, CXCL10, and clusterin, can be used to calculate the composite value. In some embodiments, clinicodemographic features are included to refine the functional score, including age and gender. In a specific case, the score may take the form of c*ADMA/(d*SDMA+age*creatinine), where c and d are specific constants, ADMA and SDMA are measured in μM, age is measured in years, and creatinine is measured in mg/dL. In some embodiments, the constants c and d are $3.932*10^4$ and 149.3 respectively, in which case the score approximates the eGFR. In some embodiments, an eGFR less than 120 mL/min per 1.73 $m^2$, less than 110 mL/min per 1.73 $m^2$, less than 100 mL/min per 1.73 $m^2$, less than 95 mL/min per 1.73 $m^2$, less than 90 mL/min per 1.73 $m^2$, less than 85 mL/min per 1.73 $m^2$, less than 80 mL/min per 1.73 $m^2$, less than 75 mL/min per 1.73 $m^2$, less than 70 mL/min per 1.73 $m^2$, less than 65 mL/min per 1.73 $m^2$, less than 60 mL/min per 1.73 $m^2$, less than 55 mL/min per 1.73 $m^2$, less than 50 mL/min per 1.73 $m^2$, less than 45 mL/min per 1.73 $m^2$, less than 40 mL/min per 1.73 $m^2$, less than 35 mL/min per 1.73 $m^2$, or less than 30 mL/min per 1.73 $m^2$ is indicative of kidney injury status. In some embodiments, an eGFR less than 90 mL/min per 1.73 $m^2$ indicates the subject has reduced kidney function or kidney disease.

In some embodiments, the functional score is calculated based on the following equation: SDMA+83.321*A−D+E, where A is the minimum of B or ($SDMA^2$*C/(age*ADMA)) where B is 1 if (37*ADMA)>=total protein and 0 otherwise, where C is minimum of 0.288 or citrate, where D is the minimum of total protein or 48.065+ADMA or creatinine, and where E is (277+140*ADMA)($Gender_F$+SDMA), where $Gender_F$=1 if the Gender is female. In this case, ADMA, SDMA, and citrate are measured in μM, age is measured in years, total protein is measured in ug/mL, and creatinine is measured in mg/dL. (See FIG. 2D).

Figure 2E:
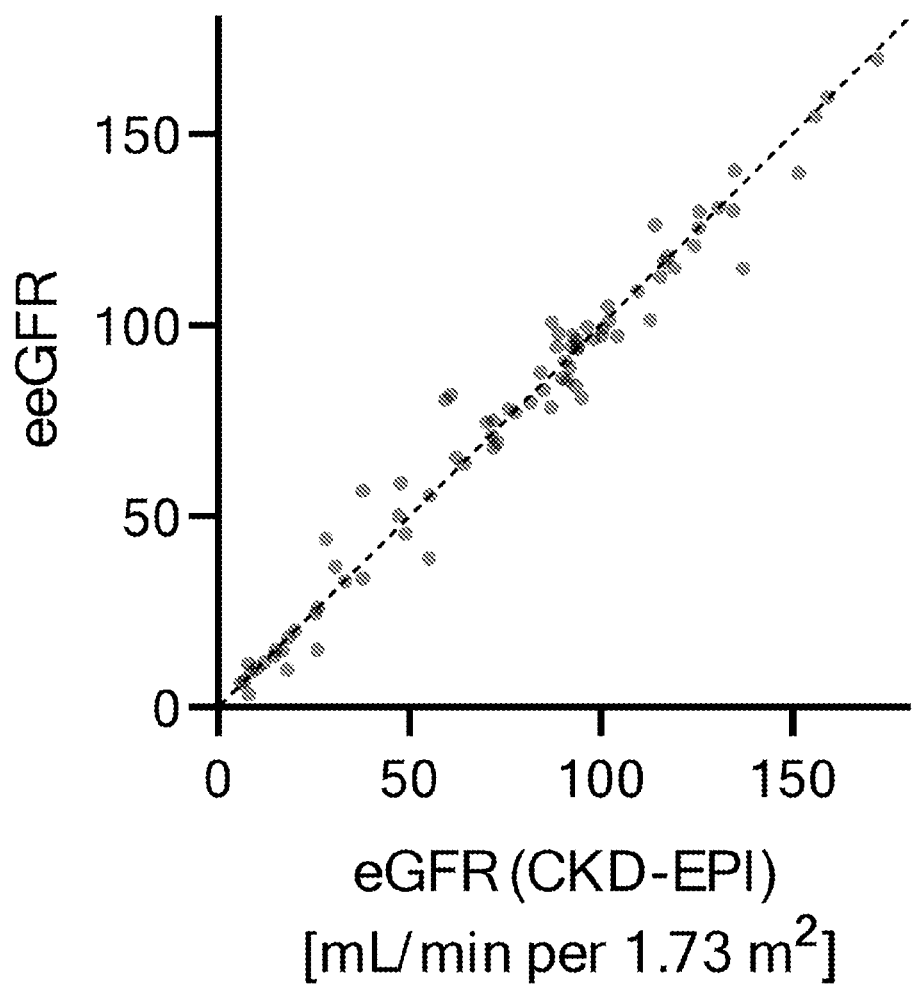
FIG. 2E shows that a representative multiple linear regression can be used to determine kidney function in a patient. The data in FIGS. 1A-2E are from a dataset of 80 urine samples.

In some embodiments, a multiple linear regression of the above parameters can be used in order to create a functional score. In some embodiments, an intercept is included. In some embodiments, two-way interactions, three-way interactions, and transforms such as logarithm, square, cube, and square root are included (FIG. 2E). In some embodiments, logistic regression or bootstrap random forest ensemble models are used to determine a functional score. The present disclosure contemplates variations of the analysis that can be similarly used to transform the data into a functional score.

Figure 3:
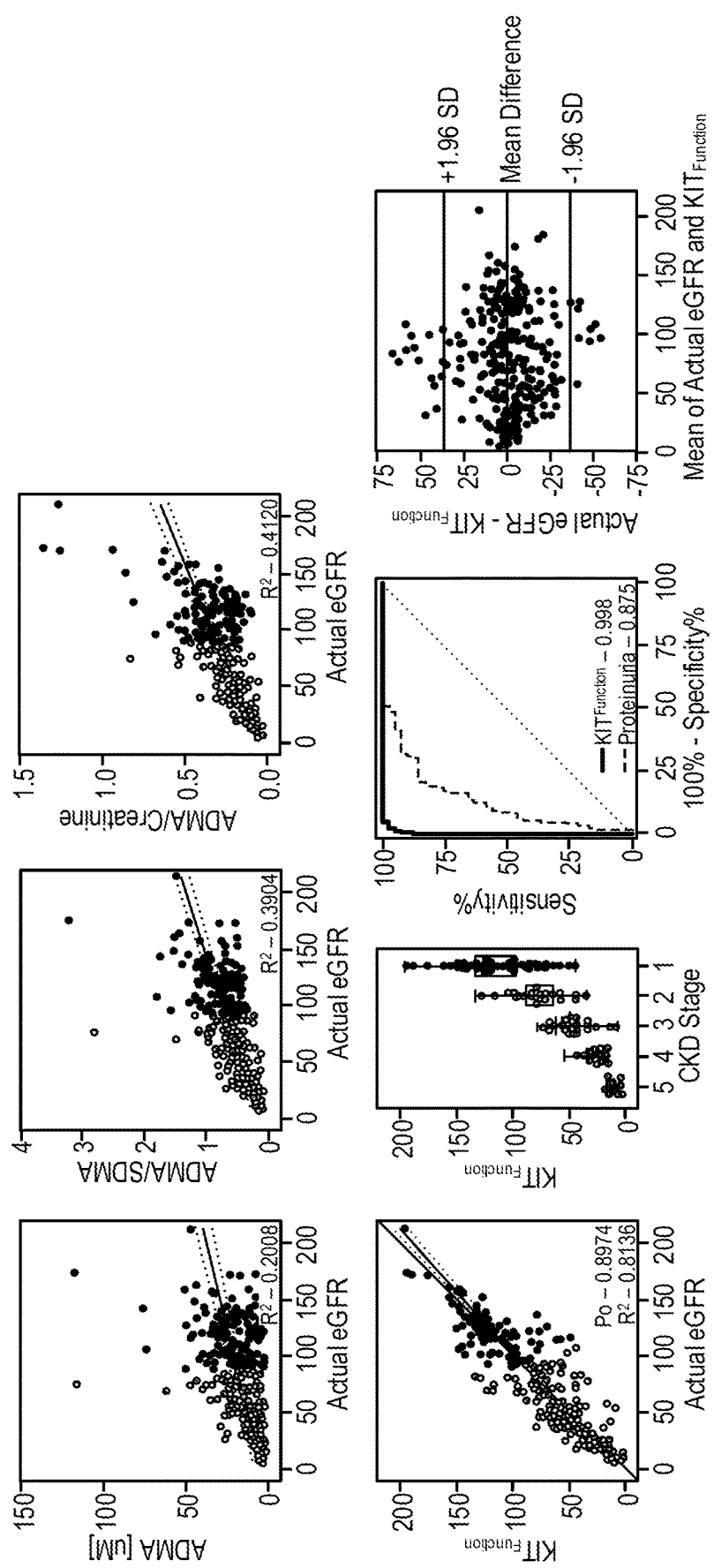
FIG. 3 shows data from a larger data set of 300 urine samples. Based on these data. $KIT_{Function}$ (also referred to as $KIT_{GFR}$) was calculated using a formula that incorporates SDMA, ADMA, urine creatinine, urine protein and age of patient. The upper row of panels shows eGFR plotted against ADMA concentration, the ratio of ADMA/SDMA, and the ratio of ADMA to creatinine. The lower row of panels shows eGFR plotted against $KIT_{Function}$, CKD stage plotted against $KIT_{Function}$, specificity and sensitivity of the assay for $KIT_{Function}$ and proteinuria, and mean of actual eGFR and $KIT_{Function}$ versus actual eGFR minus $KIT_{Function}$.

In some embodiments, kidney function ($KIT_{Function}$ or $KIT_{GFR}$) is calculated using a formula that incorporates ADMA, and a marker of hydration that can be either SDMA or urine creatinine. The formula can further incorporate the biological gender and age of patient. The formula can also incorporate the total amount of protein. Additional model development can also include gender and race (FIG. 3). In some instances a race of the subject is not inputted into the algorithm. In some embodiments, the following formula is used to calculate $KIT_{GFR}$: $KIT_{GFR}$=141.922734943398+44.1991850006697*ADMA/Creatinine−max(Age, min (150.839900231942+−200.429015237454*ADMA/Creatinine−ADMA, Age*Protein−1403.95919636272−Creatinine*ADMA)).

Figure 5A:
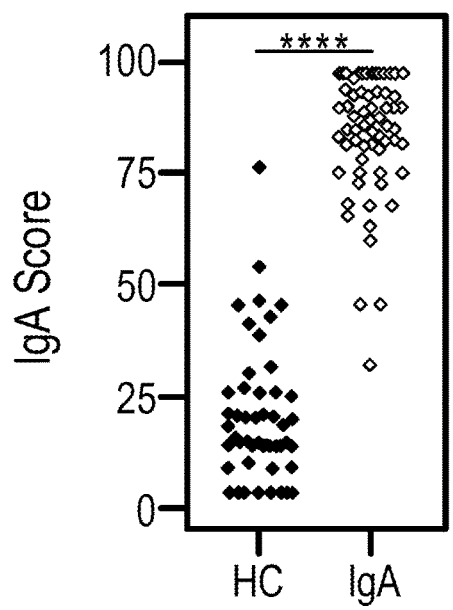
FIGS. 5A and 5B show that the urinary KIT biomarkers could segregate healthy controls from those with IgA nephropathy.
Figure 5B:
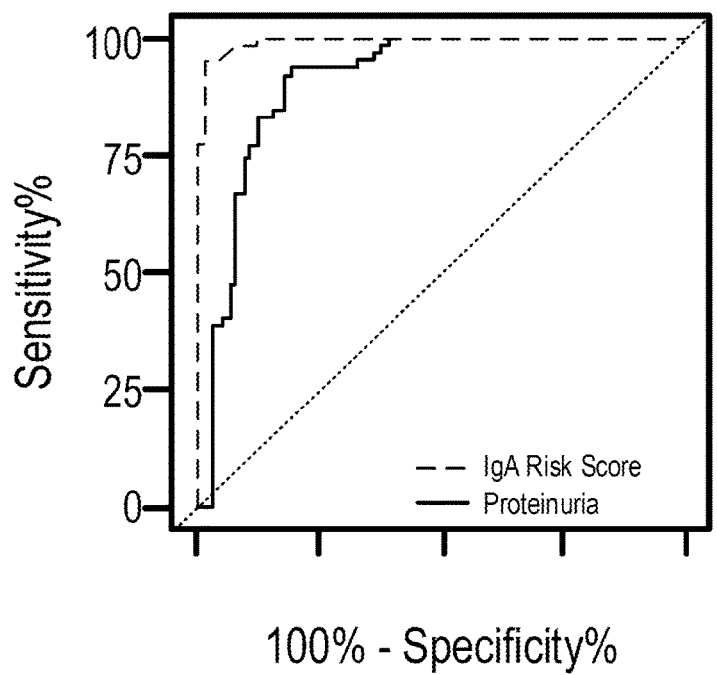

Kidney function and injury are related, but injury can occur at severely low function or at normal function. Acute kidney injury (AKI), formerly called acute kidney failure, for example can be associated with a sudden decline in glomerular filtration rate (GFR). The assays and biomarkers described herein can also be used to discriminate healthy control subjects from patients with IgA nephropathy. As shown in the FIGS. 5A and 5B, an IgA risk score was developed using the biomarkers using a Bootstrap Forest ensemble model, as described in the Examples. For the IgA Risk Score, at a threshold of 57.4, the sensitivity and specificity were 95.5% and 98.4% respectively.

Figure 6:
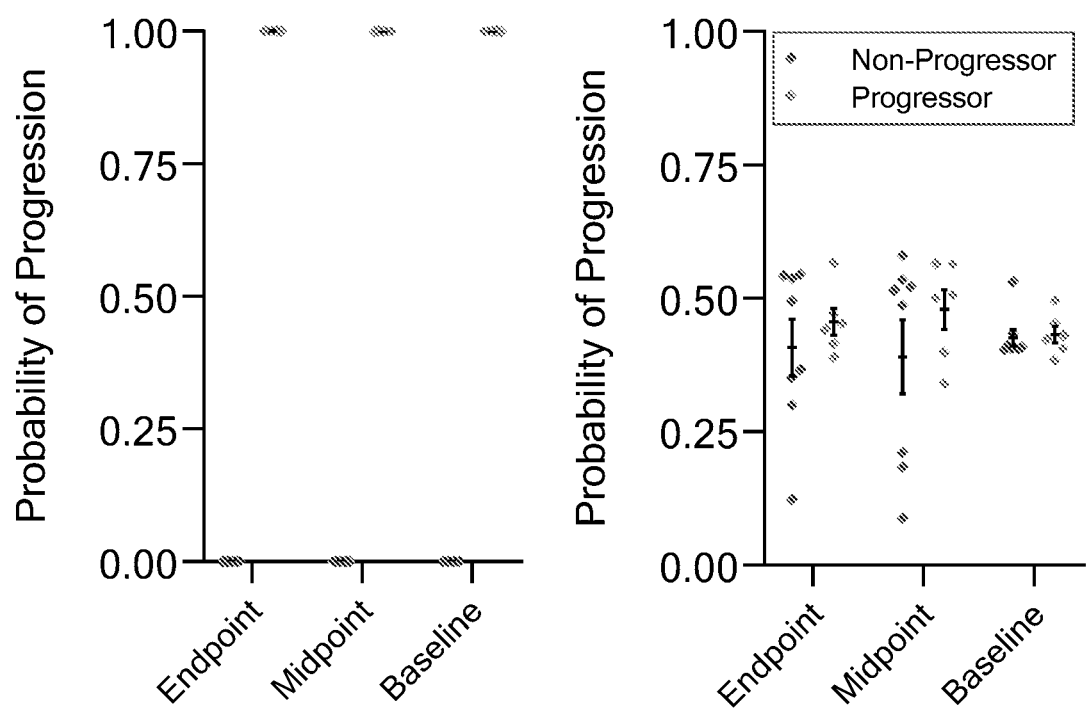
FIG. 6 shows a representative example of biomarker modeling of disease progression status after one year of treatment. Modeling was performed on endpoint, midpoint, and baseline biomarker data. The y-axis shows the probability of progression as determined by a nominal logistic regression model.

The assays and biomarkers described herein can also be used discriminate kidney disease progressors from non-progressors. As shown in FIG. 6, urinary biomarkers alone could be used to classify progressor status. In some embodiments, progressor status was classified using nominal logistic regression with 100% accuracy based on urinary measurements alone (P=0.0154).

Kits

Also provided are kits that can be used to detect kidney function in a subject. In some embodiments, the kit comprises reagents for detecting ADMA and SDMA in a urine sample. In some embodiments, the reagents comprise antibodies that specifically bind ADMA and SDMA.

In some embodiments, the kit comprises a coupling agent. In some embodiments, the coupling agent is selected from N-hydroxysuccinimido carbonic acid; (2,5-dioxopyrrolidin-1-yl) hydrogen carbonate (also known as succinimidocarbonate); N,N'-Disuccinimidyl carbonate; carbonic acid (chloromethyl ester) (N-hydroxysuccinimide ester); or (2,5-dioxopyrrolidin-1-yl) prop-2-enyl carbonate.

In some embodiments, the kit further comprises reagents for detecting one or more additional biomarkers in a urine sample, such as citrate, creatinine, total protein, 5-methylcytosine, cell-free DNA, methylated cell-free DNA, CXCL10, or clusterin.

In specific embodiments, provided herein is a kit for use in detecting kidney function in a subject, the kit comprising: an antibody for detecting ADMA; a reagent for covalent conjugation to ADMA; and a reagent for assessing hydration status of the subject. In some instances, the kit further comprises a detection reagent for detecting total urinary protein, an antibody for detecting ADMA that has a reactivity for symmetric dimethylarginine (SDMA) that is less than 25%, less than 10%, less than 5%, or less than 1% of its reactivity for ADMA. In some cases the reagent for covalent conjugation to ADMA is selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In other cases the kit further comprising a reagent for binding to cell-free DNA, a reagent for binding to CXCL10, a reagent for binding to creatinine, a reagent for binding to 5-methyclytosine, a reagent for binding to methylated cell-free DNA, a reagent for binding to clusterin, a receptacle for containing a urine sample.

In specific instances, the reagents are part of a lateral flow device and are used in a lateral flow assay. Also described herein is a lateral flow assay (LFA) platform for the detection and quantification of analytes in complex mixtures, where the sample is placed on a LFA device and the results are displayed within less then 30 min. An LFA-based test of the disclosure can be used for the qualitative and quantitative detection of specific antigens, nucleic acids, antibodies, as well as products of gene amplification, including, but not limited to cell-free DNA (cfDNA), 5-methylcytosine, CXCL10, clusterin, albumin, creatinine, total protein, amongst others. A variety of biological samples can be tested using LFAs, including urine, saliva, sweat, serum, plasma, whole blood, and other fluids.

Reaction Mixtures

Also provided are reactions mixtures comprising a urine sample, a coupling agent, and antibodies that specifically bind ADMA and SDMA. In some embodiments, the coupling agent is N-hydroxysuccinimido carbonic acid.

In some instances, the disclosure provides a reaction mixture comprising: a urine sample of a subject, a reagent for covalent conjugation to ADMA, and an antibody to ADMA. The reaction mixture may also have a reagent for covalent conjugation to ADMA is selected from N-hydrosuccinimido carbonic acid; (2,5-dioxopyrrolidin-1yl)hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl)prop-2-enyl carbonate. In some instances, the antibody to ADMA has a reactivity for symmetric dimethylarginine (SDMA) that is less than 25%, less than 10%, less than 5%, or less than 1% of its reactivity for ADMA.

Methods of Treatment

Also provided are methods of treating a disease or disorder associated with decreased kidney function or kidney disease in a subject. In some embodiments, the subject is an animal such as a mammal, a companion animal (dog, cat, or other companion animal), or a human. In some embodiments, the methods comprise identifying or selecting a subject for treatment based on the amount or concentration of ADMA in a urine sample. In some embodiments, the methods comprise identifying or selecting a subject for treatment based on the amount or concentration of ADMA and SDMA in a urine sample. In some embodiments, the subject is selected for treatment if the amount or concentration of ADMA in the urine sample is below a threshold value. In some embodiments, the subject is selected for treatment if the amount or concentration of ADMA and SDMA in the urine sample is below a threshold value. In some embodiments, the threshold value is determined as described above. In some embodiments, the threshold ADMA concentration is 19.421 µM (i.e., an ADMA value less than this value indicates the subject has reduced kidney function associated with kidney disease). In some embodiments, the threshold ADMA value corresponds to an eGFR of less than 90 mL/min per 1.73 m$^2$. In some embodiments, an eGFR value of less than 90 indicates the subject has reduced kidney function or kidney disease. Thus, in some embodiments, a subject is selected for treatment if the eGFR value is less than 90 mL/min per 1.73 m$^2$.

In some embodiments, the subject is selected for treatment based on the ratio of ADMA/creatinine in the sample. In some embodiments, the subject is selected for treatment if the ADMA/creatinine ratio is less than 0.312 (µM/mg/dL). In some embodiments, an ADMA/creatinine ratio less than 0.312 (µM/mg/dL) indicates the subject has reduced kidney function or kidney disease.

In some embodiments, the subject is selected for treatment based on the ratio of ADMA/SDMA in the sample. In some embodiments, the subject is selected for treatment if the ADMA/SDMA ratio is less than 0.694. In some embodiments, an ADMA/SDMA ratio less than 0.694 indicates the subject has reduced kidney function or kidney disease.

In some embodiments, a method of treating a disease associated with decreased kidney function in a subject is provided, the method comprising the steps of: (a) selecting a subject having decreased kidney function as determined by (i) an ADMA concentration less than 19.421 µM; or (ii) an ADMA/creatinine ratio less than 0.312 (µM/mg/dL); or (iii) an ADMA/SDMA ratio less than 0.694; or (iv) an eGFR less than 90 mL/min per 1.73 m$^2$; or (v) a $KIT_{GFR}$ less than 90 mL/min per 1.73 m$^2$; and (b) administering a treatment to the subject.

In some embodiments, the disease associated with decreased kidney function is kidney disease. In some embodiments, the disease associated with decreased kidney function is chronic kidney disease.

In some embodiments, the amount or concentration ADMA and SDMA in a urine sample is used to determine kidney function. In some embodiments, the amount or concentration ADMA and SDMA in a urine sample is used to approximate eGFR. In some embodiments, additional biomarkers are used to determine kidney function in the subject. In some embodiments, the additional biomarkers are selected from one or more of citrate, creatinine, total protein, 5-methylcytosine, cell-free DNA, methylated cell-free DNA, CXCL10, or clusterin, or combinations thereof.

After a subject is selected or identified as having decreased kidney function using the methods described herein, and appropriate treatment therapy can be determined by a health care professional. The treatment can comprise administering a pharmaceutically effective amount of a pharmaceutical drug, agent or compound to the subject. Pharmaceutically effective amounts can be determined by a health care professional, such as a physician, based on the specific condition or disease presented by each patient. For example, if the subject is diagnosed with IgA/Non-IgA mesangial proliferative glomerulonephritis, or membranoproliferative glomerulonephritis, the subject can be treated with a steroid therapy, such as methylprednisone or prednisolone.

In some embodiments, the subject may have one or more additional disorders or diseases that contribute to reduced kidney function, such as diabetic kidney disease. If a subject is diagnosed with diabetic kidney disease, the subject can be treated with an effective amount of a drug or compound appropriate for diabetic kidney disease, such as the SGLT-2 receptor inhibitor empaglifozin. a SIRT1 agonist, or a bromodomain inhibitor.

In some embodiments, the methods described herein can be used to determine kidney function associated with kidney disease or a particular stage of CKD. In some embodiments, the subject is treated by dialysis if the methods described herein identify the subject as having stage 5 CKD.

In some embodiments, administering the treatment comprises administering a diabetic kidney disease-targeted drug, a SGLT-2 receptor inhibitor, a SIRT1 agonist, or a bromodomain inhibitor to the subject if the subject is diagnosed with diabetic kidney disease. In some instances, administering the treatment comprises administering a steroid therapy to the subject if the subject is diagnosed with IgA/Non-IgA mesangial proliferative glomerulonephritis or membrano-proliferative glomerulonephritis. In other cases, the treatment comprises dialysis.

Specifically, diabetic nephropathy is a serious kidney-related complication of type 1 diabetes and type 2 diabetes. It is also called diabetic kidney disease. About 25% of people with diabetes eventually develop kidney disease. Diabetic nephropathy affects the kidneys' ability to do their usual work of removing waste products and extra fluid from your body. In some instances, the methods provided herein further contemplate administering a treatment plan that may include various medications for treatment of diabetic nephropathy, such as those that help:

a) Control high blood pressure. Medications called angiotensin-converting enzyme (ACE) inhibitors and angiotensin II receptor blockers (ARBs) are used to treat high blood pressure. Using both of these together isn't advised because of increased side effects. Studies support the goal of a blood pressure reading below 140/90 millimeters of mercury (mm Hg) depending on your age and overall risk of cardiovascular disease;

b) Manage high blood sugar. Several medications have been shown to help control high blood sugar in people with diabetic nephropathy. Studies support the goal of an average hemoglobin A1C of less than 7%. SGLT2 is the major cotransporter involved in glucose reabsorption in the kidney. SGLT2 is located in the early proximal tubule, and is responsible for reabsorption of 80-90% of the glucose filtered by the kidney glomerulus. In some instances, administering the treatment comprises administering a SGLT-2 receptor inhibitor to the subject;

c) Lower high cholesterol. Cholesterol-lowering drugs called statins are used to treat high cholesterol and reduce protein in the urine;

d) Foster bone health. Medications that help manage calcium phosphate balance are important in maintaining healthy bones. Examples of medications that regulate calcium phosphate balance include calcium-based phosphate binders, and noncalcium-, nonaluminum-, and nonmagnesium-containing phosphate binding agents (such as sevelamer HCl); and e) Control protein in urine. Medications can often reduce the level of the protein albumin in the urine and improve kidney function. Examples of medications that reduce protein in urine include angiotensin-converting enzyme (ACE) inhibitors and angiotensin receptor blockers (ARBs).

Kidney Injury Status

Compositions and methods are provided that can be used to assess kidney injury status, i.e., the presence or absence of kidney injury in an individual. Such an assessment is helpful for diagnosing when an individual is in need of medical intervention, such as being given more medication to address the medical problem or having medication decreased (including cessation) where it is no longer medically necessary. For example, compositions and methods described herein can be used to determine when an individual has kidney injury due to kidney transplant or kidney disease.

Kidney injury can develop in patients who have undergone a kidney transplant. This can happen because of several immune and non-immune factors such as ischemia reperfusion injury, size disparity, donor related factors, cell-mediated rejection, and antibody-mediated rejection, by way of example. Problems after a transplant may include: transplant rejection (hyperacute, acute or chronic), infections and sepsis due to the immunosuppressant drugs that are required to decrease risk of rejection, post-transplant lymphoproliferative disorder (a form of lymphoma due to the immune suppressants), imbalances in electrolytes including calcium and phosphate which can lead to bone problems among other things, and other side effects of medications including gastrointestinal inflammation and ulceration of the stomach and esophagus, hirsutism (excessive hair growth in a male-pattern distribution), hair loss, obesity, acne, diabetes mellitus type 2, hypercholesterolemia, and osteoporosis.

Kidney injury can also develop in patients having kidney disease. Kidney diseases are diverse, but individuals with kidney disease frequently display characteristic clinical features. Common clinical conditions involving the kidney include but are not limited to the nephritic and nephrotic syndromes, renal cysts, acute kidney injury, chronic kidney disease, diabetes-induced nephropathy, urinary tract infection, nephrolithiasis, and urinary tract obstruction, glomerular nephritis (GN), focal segmental glomerular sclerosis (FSGS), IgA nephropathy (IgAN), mesangiocapillary, lupus, membranous, hypertensive nephropathy, and drug induced nephropathy. Kidney diseases can also include the various cancers of the kidney which exist. For example such cancers include, but are not limited to, renal cell carcinoma, urothelial cell carcinoma of the renal pelvis, squamous cell carcinoma, juxtaglomerular cell tumor (reninoma), angiomyolipoma, renal oncocytoma, bellini duct carcinoma, clear-cell sarcoma of the kidney, mesoblastic nephroma, Wilms' tumor, mixed epithelial stromal tumors, clear cell adenocarcinoma, transitional cell carcinoma, inverted papilloma, renal lymphoma, teratoma, carcinosarcoma, and carcinoid tumor of the renal pelvis. Kidney disease can also be virally induced and include, but are not limited to BKV nephropathy and nephropathy induced by EBV and CMV. Kidney disease can also be drug-induced as some medications are nephrotoxic (they have an elevated risk for harming the kidneys). In the worst case, the drug causes kidney failure, while in other cases, the kidneys are damaged, but do not fail. Common nephrotoxic drugs include, but are not limited to, nonsteroidal anti-inflammatory drugs (NSAIDs), some antibiotics, some painkillers, and radiocontrast dyes used for some imaging procedures.

In some embodiments, a urine sample is from an individual having a kidney transplant, or one of the above-listed kidney disorders or kidney transplant clinical conditions described above is assayed as described herein.

EXAMPLES

Example 1

This example describes a representative assay of the methods described herein. The assay was performed based on the following protocol:

1. Raw urine samples received by the lab are collected in standard urine collection containers (100 mL maximum volume)
2. The urine specimen is equally aliquoted into 50 mL conical tubes.
3. The urine is centrifuged for 20 minutes at 2,000×g at 4° C.
4. The urine is pooled into a separate container and the pellet discarded. This removes contaminating debris and cells. Alternatively, a 5 micron (μM) cell strainer may be employed to similar effect.
5. Tris 1M pH 7.0 is added to the pooled urine at 1/10th volume of the urine. This ensures that all samples will behave similarly in the downstream analysis procedures and ensures similar stability of urine components.
6. For long-term storage (>1 month), the sample is stored at −80° C. For short-term storage prior to analysis, the sample is stored at −20° C.
7. For the ADMA ELISA, the urine is diluted 1:20 in 1×PBS to ensure proper osmolality for downstream derivatization and antibody binding.
8. 1× PBS with 0.05% Tween-20 is used as the wash buffer (PBST).
9. For each sample, 50 tit of the pre-diluted urine is mixed with 150 μL of 1 M Tris-HCl, pH 9.1. To this, 50 μL of the derivatization solution (0.833 mg of N-hydroxysuccinimido carbonic acid in 50 μL of DMSO) is mixed on a horizontal shaker at 400 RPM for 45 minutes at room temperature. Standards (diluted from stock solution in 1×PBS) are treated similarly.
10. 250 μL of 1×PBS is added to the mixture and mixed on a horizontal shaker at 400 RPM for 45 minutes at room temperature.
11. Onto a clear-bottom, functionalized ELISA microplate which has been coated with BSA conjugated to ADMA, 50 μL of the derivatized samples are added.
12. 50 μL of mouse monoclonal ADMA IgM antibody is added to each of the wells and allowed to incubate overnight at 4° C.
13. The wells are washed 5× with PBST.
14. 100 μL of biotinylated rabbit anti-mouse IgM is added to each of the wells and allowed to incubate for 1 hour at RT at 400 RPM on a horizontal shaker.
15. The wells are washed 5× with PBST.
16. 100 μL of 1-Step Ultra TMB-ELISA Substrate Solution is added and covered with a foil plate cover.
17. The plate is allowed to incubate for ~15 minutes at RT at 400 RPM on a horizontal shaker.
18. 100 μL of 2N sulfuric acid is added to each well.
19. Absorption is determined by using a colorimetric plate reader at 450 nm with 620 nm as a reference wavelength.
20. A 4-parameter logarithmic fit is used to interpolate the unknown values against the standard curve values.

Example 2

This example describes a representative study design and patient disposition.

Figure 4:
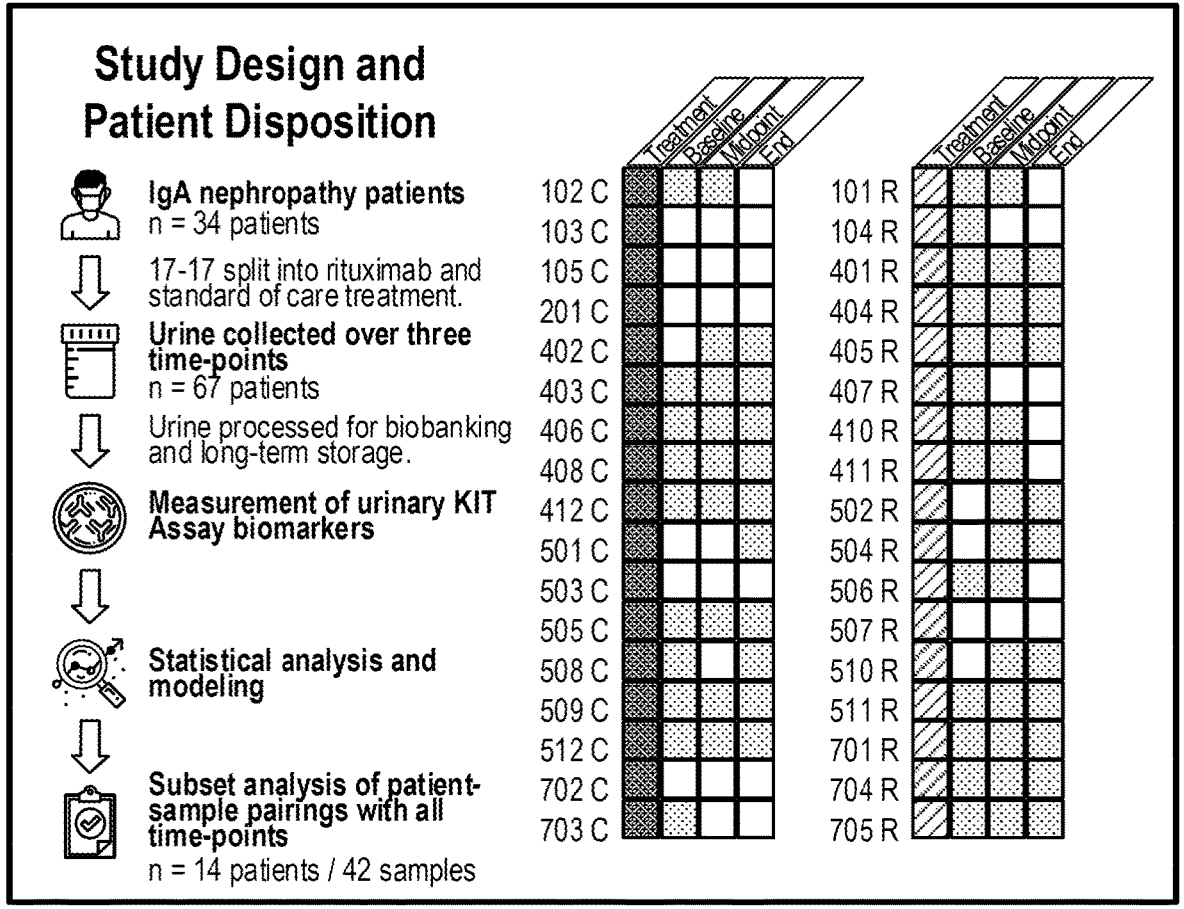
FIG. 4 shows a representative study design and patient disposition. (Left) In the original trial, 34 patients met inclusion criteria and were randomized into rituximab and standard of care treatment groups. At least one urine sample was available from 28 of the 34 patients, with 14 having urine samples at all three designated time-points. (Right) Pictorial depiction of patients, treatment, and sample availability. Patients were segregated based on treatment, either with standard of care (turquoise) or rituximab (coral), with individual patients as rows. A yellow square indicates a urine sample was available at the indicated time-point, while gray indicates that no urine sample was available.

From 34 total patients, 69 urine samples were collected from 28 patients (FIG. 4). Two time-points or more was available from 25 patients, and a complete set of three time-points collected at baseline, ½ year, and 1 year was available from 14 patients. The baseline characteristics and disposition of the 14 patients are listed in Table 1.

TABLE 1

| Baseline characteristics of IgA nephropathy patients with urine collected at all designated three time-points. ||
|---|---|
| Baseline Characteristics | IgA Cohort (N = 14)[1] |
| Age, year | 39.5 (29-59) |
| Sex | |
| Female | 4 |
| Male | 10 |
| Race | |
| Caucasian | 7 |
| Asian/Pacific Islander | 5 |
| Hispanic/Latino | 2 |
| BMI, kg/m$^2$ | 27.9 (20.5-37.4) |
| eGFR, mL/min per 1.73 m$^2$ | 44.7 (30.6-69.3) |
| Treatment | |
| Rituximab | 7 |
| Standard of Care | 7 |

[1]Data are reported as median (range) or count.

There was no statistically significant difference between the change in eGFR over the course of the study by treatment with rituximab over standard of care (data not shown). However, while some patients maintained or even recovered kidney function (corresponding to an increase in eGFR), some patients had IgAN progression with functional decline. We therefore investigated whether the KIT Assay biomarkers could be used to not only detect IgA nephropathy through urine alone, but also monitor kidney function changes longitudinally.

Example 3

This example shows that the biomarkers described herein can discriminate healthy controls from patients with IgA Nephropathy.

Urine samples from healthy control patients were assessed and compared to those collected from the IgA nephropathy patients for the KIT biomarkers. An IgA Risk Score, ranging from 0 to 100, was developed on these biomarkers using a Bootstrap Forest ensemble model. The scores for each of the patients in the two groups are depicted in FIG. 4A. This Score could distinguish between healthy control (median 14.03, 95% CI 8.94-18.52) and IgA patients (median 87.76, 95% CI 83.39-90.32) (P<0.0001). Receive-operator characteristic curves (FIG. 4B) comparing the discrimination abilities of the IgA Risk Score and proteinuria identifies the IgA Risk Score (AUC 0.9935, 95% CI 0.985-1.000) as performing better than proteinuria (AUC 0.9100, 95% CI 0.855-0.965), even in this comparison against healthy control patients. For the IgA Risk Score, at a threshold of 57.4, the sensitivity and specificity were 95.5% and 98.4% respectively.

Example 4

This example shows that the biomarkers described herein can discriminate disease progressors versus non-progressors and predict disease progression.

Progression was defined as a composite clinical evaluation of changes in proteinuria and eGFR from baseline and, as such, was dependent on both urine and serum biomarker values. We first sought to investigate whether urinary biomarkers alone could be used to classify progressor status. Looking at the 1-year endpoint biomarkers (FIG. 6), progressor status could be classified using nominal logistic regression with 100% accuracy based on urinary measurements alone (P=0.0154). We then investigated whether midpoint (½ year prior to progression determination) and baseline (1 year prior) urinary biomarkers could predict progression status. We found that the KIT Assay biomarkers could predict progressor status with 100% accuracy at both time-points (midpoint P=0.0269, baseline P=0.0383). For both the baseline and midpoint predictions, the cfDNA values were the most important predictors, with chi square likelihood ratios of 25.92 and 141.98, and with P<0.0001 for both.

Example 5

This example describes a representative method for selecting a subject for treatment using the methods described herein.

The disclosed assay, alongside blood glucose and HbA1c testing, can be performed in a community clinic as part of a screening program targeting low resource individuals. The results of the assay may show that a patient has a $KIT_{Function}$ (a measure of kidney function which approximates eGFR) of 22 mL/min/1.73 m². Confirmatory serum creatinine results confirm that the eGFR is in the range of 15-30 mL/min/1.73 m², which is clinically recognized as Stage 4 CKD. The patient's blood glucose and HbA1c testing may also reveal that the patient has longstanding, untreated Type II diabetes. The patient will thus be diagnosed with diabetic kidney disease. The patient can be treated with a DKD-targeted drug, such as the SGLT-2 receptor inhibitor empaglifozin at the usually prescribed levels. The patient's kidney function can stabilize and the disclosed assay can be used as a monitoring tool to ensure maintenance of this kidney function over time.

Example 6

This example describes another representative method for selecting a subject for treatment using the methods described herein.

The disclosed assay can be performed as part of a nationwide screening program in primary school age children targeted towards early detection of IgA/Non-IgA mesangial proliferative glomerulonephritis as well as membrano-proliferative glomerulonephritis. In one scenario, a child is referred with a low $KIT_{Function}$ for kidney biopsy, which has confirmatory findings of IgA nephropathy as based on the Oxford classification with concurrent nephrotic syndrome. The patient is prescribed and receives pulse steroid therapy consisting of i.v. methylprednisone 500 mg/m² for 3 consecutive days. Continued oral steroid therapy consists of prednisolone of 30 mg/m² daily. Additionally, this patient could receive supportive care of a renin angiotensin system blockade. Recovery of kidney function in the patient can assessed by both an increase in eGFR/serum creatinine and the $KIT_{Function}$.

Example 7

This example describes another representative method for selecting a subject for treatment using the methods described herein.

The disclosed assay can be performed on a patient presenting with extreme fatigue, loss of appetite, vomiting, nausea, and changes in urination volume. The results of the assay may show that the patient has a $KIT_{Function}$ of 8 mL/min/1.73 m², indicating Stage 5 CKD. The patient will start renal replacement therapy, involving dialysis at an in-center dialysis clinic, where the patient receives nocturnal dialysis three times a week. The patient will continue this therapy while being placed on the kidney transplant waiting list.

Example 8

This example describes a LFA dipstick prototype for the reliable and accurate detection of ADMA/SDMA in addition to one, two, three, or four additional markers in human urine that have been associated with kidney injury and disease. The markers include cell-free DNA (cfDNA), 5-methylcytosine, CXCL10, and albumin. These four markers are indicative of various different kidney failure modes.

Normal ranges of cfDNA in urine range from 0 to 5000 GE/ml (where 1 GE=6.6 pg). Normal ranges of CXCL10 typically are from 0 to 50 pg/mL. Normal ranges of 5-mC typically range from ~0.7 to ~4 ng/ul. Normal ranges of albumin typically range from 0 to 8 mg/dL (i.e. 0 to 80 ug/mL).

The LFA dipstick prototype described herein is designed to detect the following minimum amounts of the four analytes combined with a threshold of ADMA:

| Analyte | Minimum concentrations |
|---|---|
| cfDNA | 3000 GE/mL |
| CXCL10 | 7.8 pg/mL |
| 5-mC | 0.5 ng |
| albumin | 1.5 ug/mL |

The results of the test are read using a benchtop lateral flow assay reader such as the Qiagen LR3 or the Axxin readers.

Example 9

This example describes a representative assay of the methods described herein conducted in ten (10) veterinary subjects. The assay was performed based on the general protocols described in examples above.

Urine samples from felines and canines with matched blood-based kidney function biomarkers were characterized for urinary ADMA, SDMA, total protein, and creatinine. Ten canines were included in this preliminary analysis for further validation of the markers in other mammalian models. Briefly, the standard-of-care test for veterinary applications, namely IDEXX test, was used to measure performance of kidney function in 10 canines. The kidney function of the canines as measured by the IDEXX SMDA test is described below:

| Animal ID | Sample Date | IDEXX SDMA [ug/dL] |
|---|---|---|
| CANINE-1003 | Jul. 1, 2020 | 15 |
| CANINE-1004 | Jul. 1, 2020 | 14 |
| CANINE-1005 | Jul. 1, 2020 | 19 |
| CANINE-1006 | Jul. 1, 2020 | 72 |
| CANINE-1007 | May 29, 2020 | 17 |
| CANINE-1009 | Jul. 10, 2020 | 14 |
| CANINE-1010 | Jul. 14, 2020 | 43 |
| CANINE-1013 | Jul. 17, 2020 | 12 |
| CANINE-1015 | Jul. 17, 2020 | 20 |
| CANINE-1016 | Jul. 17, 2020 | 12 |

Figure 8:
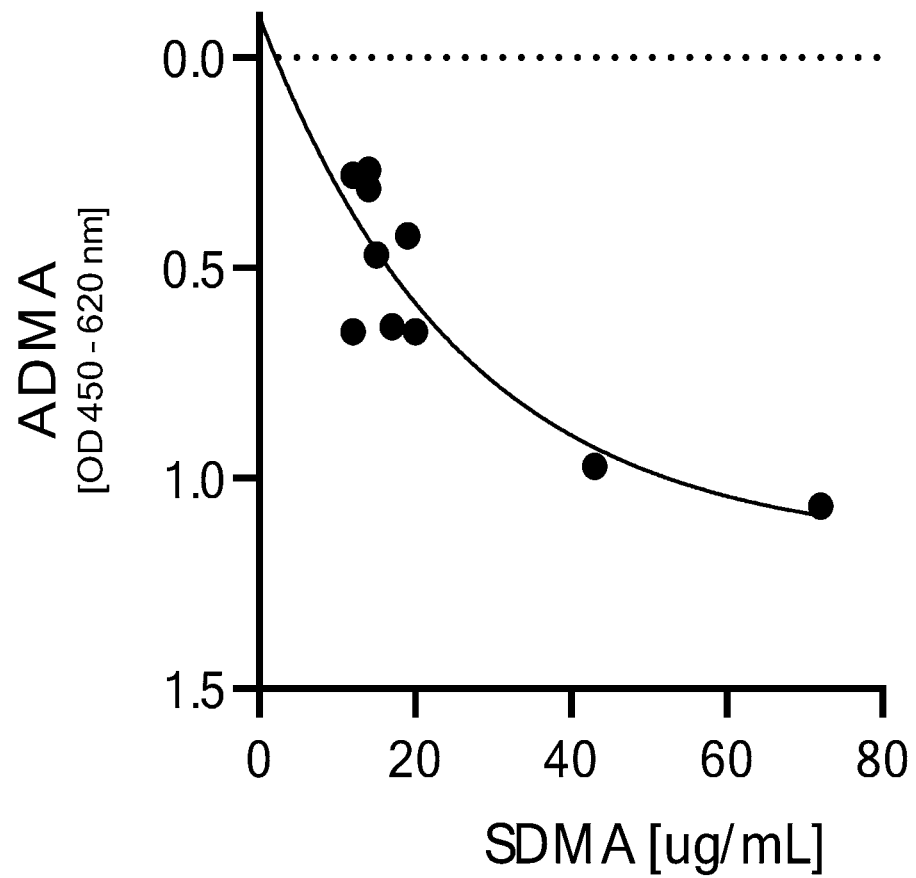
FIG. 8 shows that urinary ADMA was inversely correlated with blood SDMA in canine samples, suggesting its utility in noninvasively determining kidney function.
Figure 9:
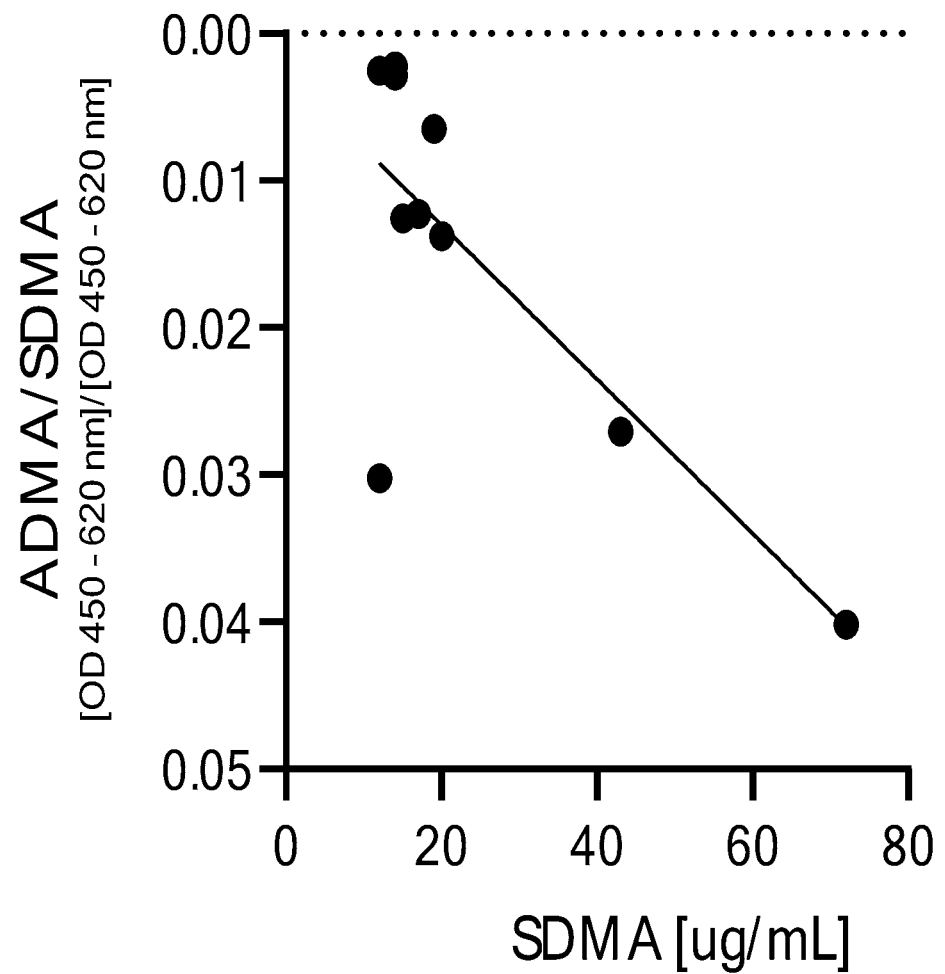
FIG. 9 shows a linear relationship between the ratio of urinary ADMA/SDMA and blood SDMA, suggesting that SDMA may be used as a normalization factor.
Figure 10:
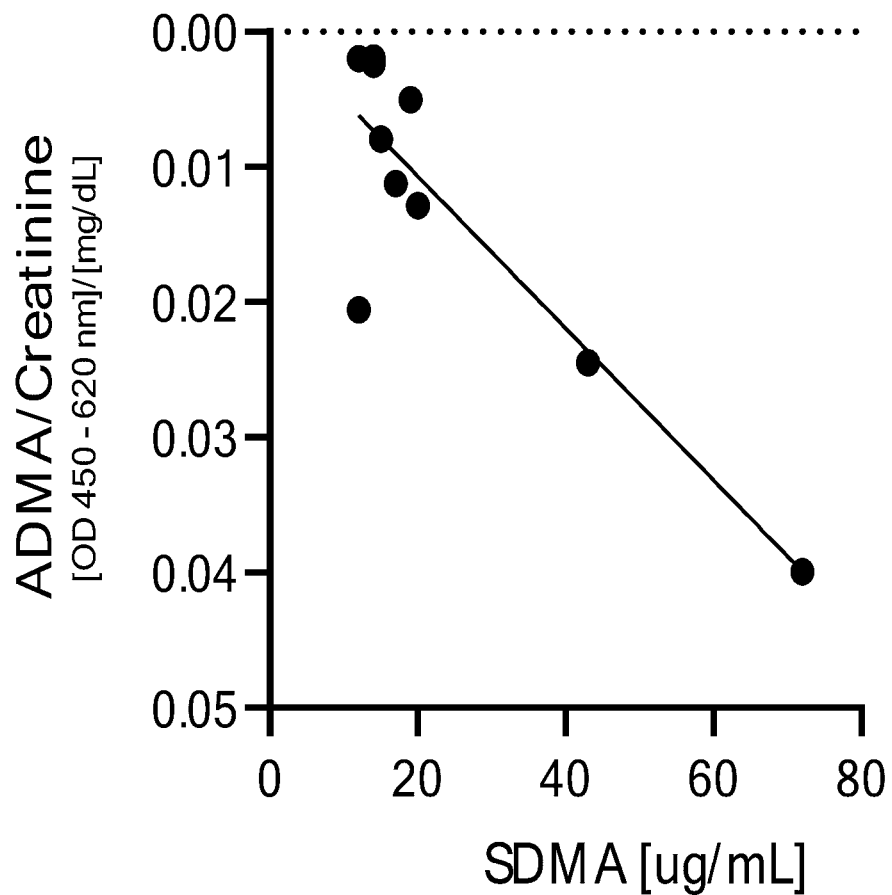
FIG. 10 shows a linear relationship between the ratio of urinary ADMA/creatinine and blood SDMA, suggesting that creatine may be used as a normalization factor.
Figure 11:
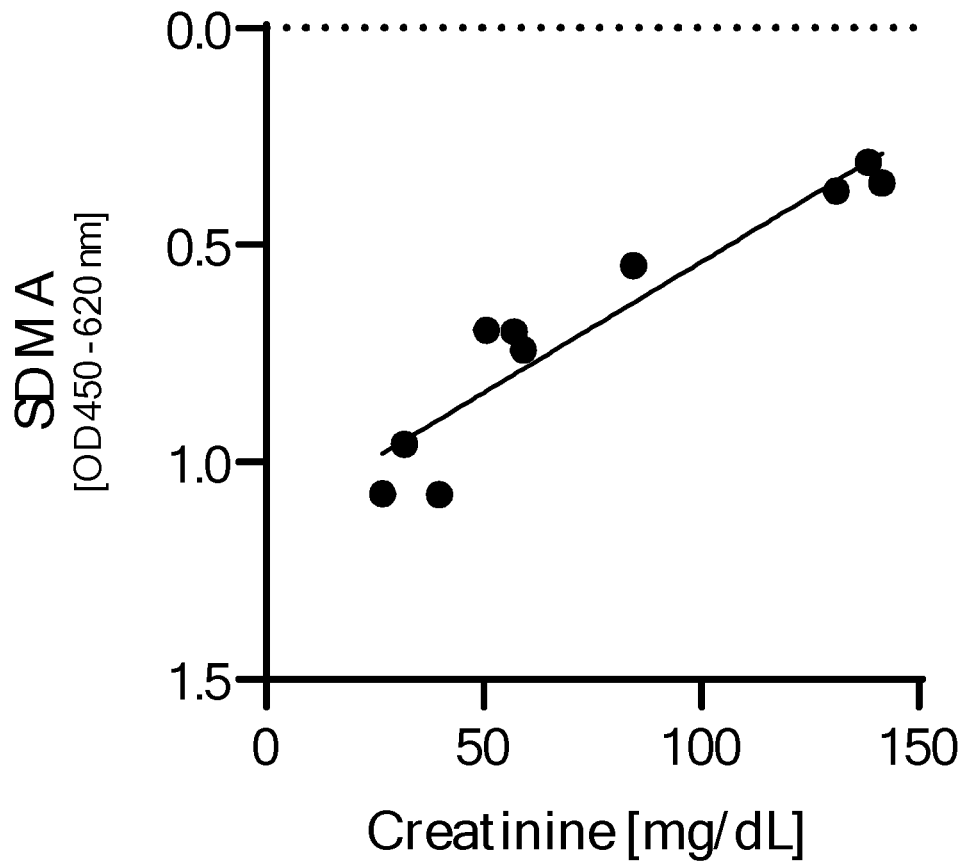
FIG. 11 shows a linear relationship between SDMA and creatinine measurements of feline and canine kidney function.

The analysis indicated that urinary ADMA was inversely correlated (exponential relationship) with blood SDMA in these canine samples, suggesting its utility in noninvasively determining kidney function. See FIG. 8. The analysis also identified a linear relationship between the ratio of ADMA/SDMA and the ratio of ADMA/SDMA with blood SDMA, demonstrating the utility of SDMA or creatinine as normalization factors. See FIG. 9 and FIG. 10. Further, SDMA and creatinine correlated strongly with one another. See FIG. 11.

Figure 12:
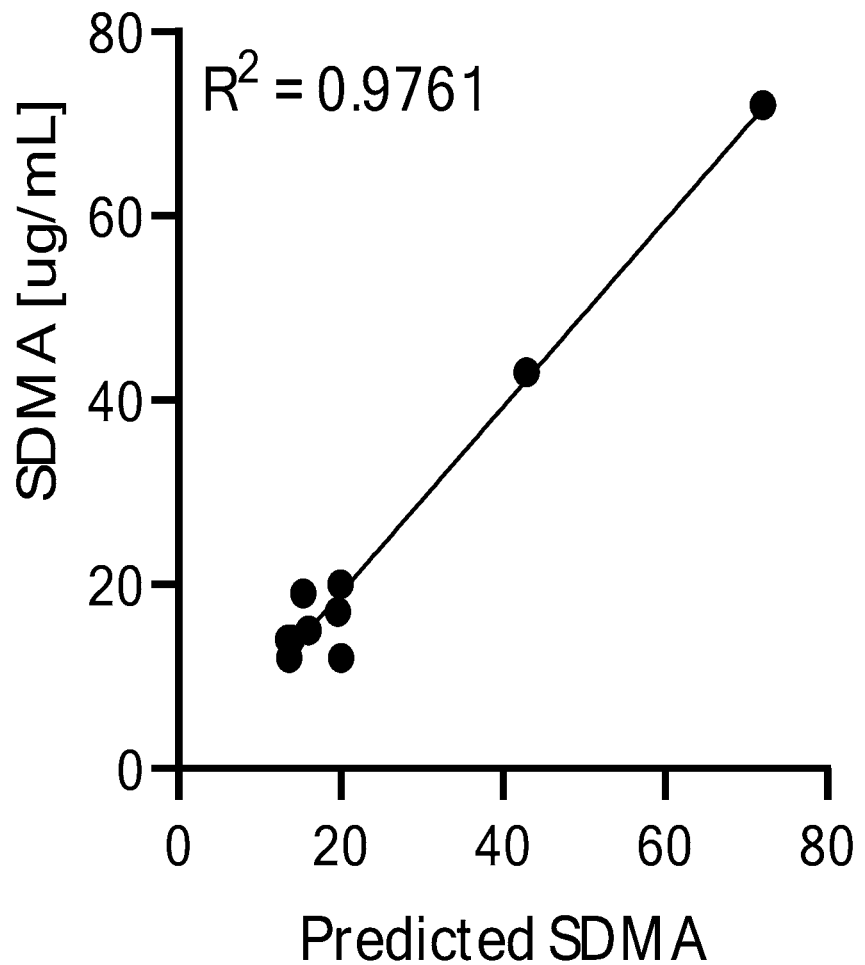
FIG. 12 is a graph illustrating the development of a one-biomarker formula only considering urinary ADMA and predicting blood SDMA.

Based on this analysis a one-biomarker formula was developed for predicting the levels of blood SDMA. See FIG. 12.

$$eGFR = 4.457 + \frac{1.290}{0.183 - 0.154 \times ADMA}$$

Figure 13:
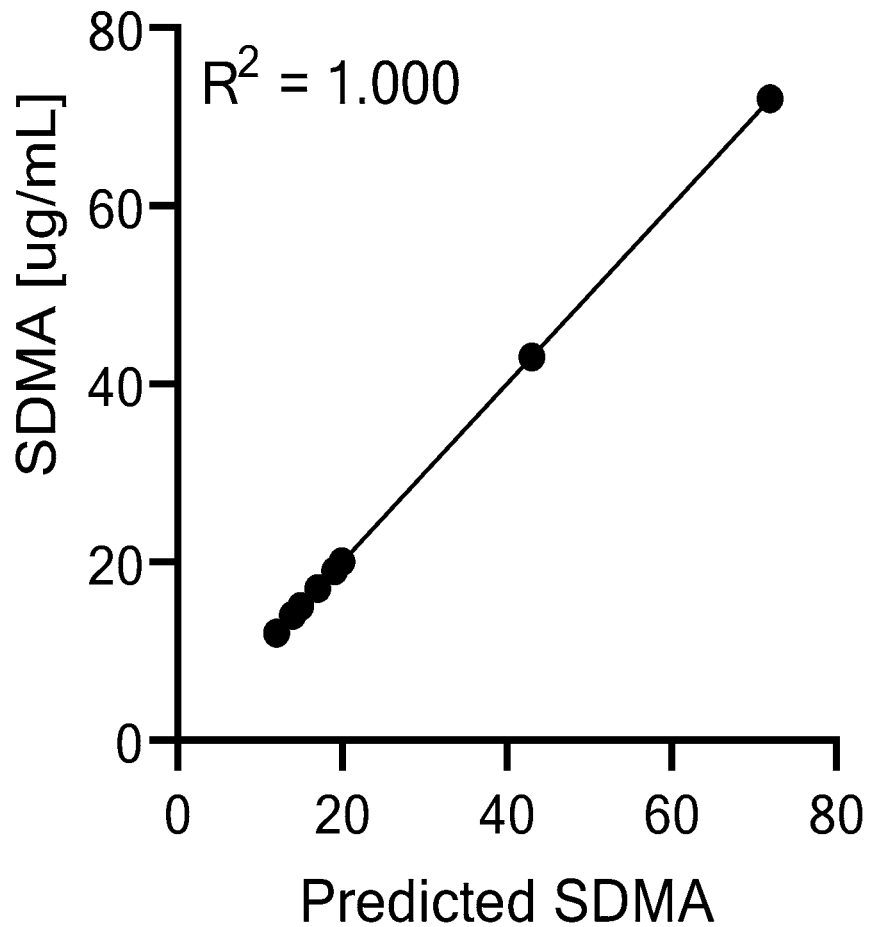
FIG. 13 is a graph illustrating the development of a formula for kidney function considering urinary SDMA, ADMA, and creatine together.

Further, a composite analysis of SDMA, ADMA, and creatine together provided the following equation for predicting the levels of blood SDMA. See FIG. 13.

$$eGFR = 12.831 + 176.293 \times SDMA + 50.745 \times ADMA + 180.145 \times ADMA^2 \times SDMA^2 - 0.137 \times CR - 0.434 \times SDMA \times CR - 230.623 \times ADMA \times SDMA - 121.514 \times SDMA^2$$

Example 10

This example describes a representative ELISA assay for the detection of SDMA. The assay is performed with antibodies purchased from Immundiagnostik AG, Stubenwald-Allee 8a, 64625 Bensheim, Germany, and resold by various suppliers, including Enzo Life Sciences. In some embodiments, detection of SDMA was performed as described below:

The assay is based on the method of competitive enzyme linked immunoassays.

The sample preparation includes the addition of a derivatisation reagent for SDMA derivatisation. Afterwards, the treated samples and the polyclonal SDMA antiserum are incubated in wells of a microtiter plate coated with SDMA derivative (tracer). During the incubation period, the target SDMA in the sample competes with the tracer, immobilised on the wall of the microtiter wells, for the binding of the polyclonal antibodies.

During the second incubation step, a peroxidase conjugated antibody is added to detect the anti-SDMA antibodies. After washing away the unbound components, tetramethylbenzidine (TMB) is added as a peroxidase substrate. Finally, the enzymatic reaction is terminated by an acidic stop solution. The colour changes from blue to yellow and the absorbance is measured in a photometer at 450 nm. The intensity of the yellow colour is inverse proportional to the SDMA concentration in the sample; this means high SDMA concentration in the sample reduces the concentration of tracer-bound antibodies and lowers the photometric signal. A dose response curve of absorbance unit (optical density, OD at 450 nm) vs. concentration is generated using the values obtained from the standards. SDMA, present in the patient samples, is determined directly from this curve.

Urine and SDMA Detection Sample Preparation Procedure

Bring all reagents and samples to room temperature (15-30° C.) and mix well. Derivatisation of standards, controls and samples is carried out in single analysis in vials (e.g. 1.5 ml polypropylene vials).

1 Add 200 µl standard (STD), 200 µl control (CTRL) and 50 µl of urine sample in the corresponding vials.
2 Add 150 µl reaction buffer (DERBUF) only to the samples.
3 Add 50 µl derivatisation reagent (DER) into each vial (STD, CTRL, sample), mix thoroughly by repeated inversion or several seconds on a vortex mixer. Incubate for 45 min at room temperature (15-30° C.) on a horizontal shaker.

2×50 µl of the derivatised standards, controls and samples are used in the ELISA as duplicates.

Test Procedure

Mark the positions of standards/controls/samples in duplicate on a protocol sheet. Take as many microtiter strips as needed from the kit. Store unused strips covered with foil at 2-8° C. Strips are stable until expiry date stated on the label.

4 For the analysis in duplicate, take 2 × 50 µl of the derivatised standards/controls/samples out of the vials and add into the respective wells of the microtiter plate.
5 Add 50 µl SDMA antibody (AB) into each well of the microtiter plate.
6 Cover the strips and incubate for 2 hours at room temperature (15-30° C.) on a horizontal shaker.
7 Discard the content of each well and wash 5 times with 250 µl wash buffer. After the final washing step, remove residual wash buffer by firmly tapping the plate on absorbent paper.
8 Add 100 µl conjugate (CONJ) into each well.
9 Cover the strips and incubate for 1 hour at room temperature (15-30° C.) on a horizontal shaker.

10 Discard the content of each well and wash 5 times with 250 µl wash buffer. After the final washing step, remove residual wash buffer by firmly tapping the plate on absorbent paper.
11 Add 100 µl substrate (SUB) into each well.
12 Incubate for 10-15 min* at room temperature (15-30° C.) in the dark.
13 Add 100 µl stop solution (STOP) into each well and mix well.
14 Determine absorption immediately with an ELISA reader at 450 nm against 620 nm (or 690 nm) as a reference. If no reference wavelength is available, read only at 450 nm. If the extinction of the highest standard exceeds the range of the photometer, absorption must be measured immediately at 405 nm against 620 nm (690 nm) as a reference.

Example 11

This example describes a representative ELISA assay for the detection of ADMA. The assay is performed with antibodies purchased from Immundiagnostik AG, Stubenwald-Allee 8a, 64625 Bensheim, Germany. In some embodiments, detection of ADMA was performed as described below:

The assay is based on the method of competitive enzyme linked immunoassays. The sample preparation includes the addition of a derivatisation-reagent for ADMA derivatisation. Afterwards, the treated samples and the polyclonal ADMA-antiserum are incubated in the wells of a microtiter plate coated with ADMA-derivative (tracer). During the incubation period, the target ADMA in the sample competes with the tracer immobilised on the wall of the microtiter wells for the binding of the polyclonal antibodies.

During the second incubation step, a peroxidase-conjugated antibody is added to detect the anti-ADMA antibodies. After washing away the unbound components, tetramethylbenzidine (TMB) is added as a peroxidase substrate. Finally, the enzymatic reaction is terminated by an acidic stop solution. The colour changes from blue to yellow, and the absorbance is measured in the photometer at 450 nm. The intensity of the yellow colour is inverse proportional to the ADMA concentration in the sample; this means, high ADMA concentration in the sample reduces the concentration of tracer-bound antibodies and lowers the photometric signal. A dose response curve of the absorbance unit (optical density, OD at 450 nm) vs. concentration is generated, using the values obtained from the standard. ADMA, present in the patient samples, is determined directly from this curve.

Sample Preparation Procedure

Bring all reagents and samples to room temperature (15-30° C.) and mix well.

Derivatisation of standards, controls and samples is carried out in single analysis in vials (e.g. 1.5 ml polypropylene vials). We recommend preparing one derivatisation per standard, control and sample and transferring it in duplicate determinations into the wells of the microtiter plate.

1 Add 200 µl standard (STD), 200 µl control (CTRL) and 50 µl urine sample in the corresponding vials.
2 Add 150 µl reaction buffer (DERBUF) only to the urine samples.
3 Add 50 µl derivatisation reagent into each vial (STD, CTRL, sample) and mix thoroughly by repeated inversion or several seconds on a vortex mixer. Incubate for 45 min at room temperature (15-30° C.) on a horizontal shaker.
4 Add 250 µl dilution buffer (CODIL) into each vial, mix well and incubate for 45 min at room temperature (15-30° C.) on a horizontal shaker.

2×50 µl of the derivatised standards, controls and samples are used in the ELISA as duplicates.

Test Procedure

Mark the positions of standards/controls/samples in duplicate on a protocol sheet. Take as many microtiter strips as needed from the kit. Store unused strips covered with foil at 2-8° C. Strips are stable until expiry date stated on the label.

5 For the analysis in duplicate take 2 × 50 µl of the derivatised standards/controls/samples out of the vials and add into the respective wells of the microtiter plate.
6 Add 50 µl ADMA antibody into each well of the microtiter plate.
7 Cover the strips tightly with foil and incubate overnight at 2-8° C.
8 Discard the content of each well and wash 5 times with 250 µl wash buffer. After the final washing step, remove residual wash buffer by firmly tapping the plate on absorbent paper.
9 Add 100 µl conjugate (CONJ) into each well.
10 Cover the strips and incubate for 1 hour at room temperature (15-30° C.) on a horizontal shaker.
11 Discard the content of each well and wash 5 times with 250 µl wash buffer. After the final washing step, remove residual wash buffer by firmly tapping the plate on absorbent paper.
12 Add 100 µl substrate (SUB) into each well.
13 Incubate for 10-14 min* at room temperature (15-30° C.) in the dark.
14 Add 100 µl stop solution (STOP) into each well and mix well.

-continued

15 Determine absorption immediately with an ELISA reader at 450 nm against 620 nm (or 690 nm) as a reference. If no reference wavelength is available, read only at 450 nm. If the extinction of the highest standard exceeds the range of the photometer, absorption must be measured immediately at 405 nm against 620 nm (690 nm) as a reference.

For automated ELISA processors, the given protocol may need to be adjusted according to the specific features of the respective automated platform.

Example 12

This example describes a representative ELISA assay for the parallel detection of ADMA and SDMA. The assay is performed with antibodies purchased from Immundiagnostik AG, Stubenwald-Allee 8a, 64625 Bensheim, Germany. In some embodiments, detection of ADMA and SDMA was performed as described below:

In these ELISAs, standards and controls are provided by the manufacturer as ready-to-use vials. The ADMA antibody and derivatization reagents come lyophilized and must be reconstituted. The SDMA antibody does not come lyophilized and is ready-to-use.

Pre-Prep

The SDMA standards are stored at −20° C. These should be removed prior to the start of the experiment to thaw.

The ADMA DMSO and the SDMA DER derivatization reagents are frozen at 4° C. These should be thawed prior to use by thawing or on a heat block.

The ADMA DER derivatization reagent is lyophilized and must be reconstituted in 6 mL of DMSO 10 minutes prior to use.

The ADMA antibody is lyophilized and must be reconstitute in 6 mL of 1× wash buffer.

Sample Preparation

Bring all reagents from both ADMA and SDMA kits and samples to room temperature (20-30° C.) and mix well. Make wash buffer by diluting wash buffer concentrate (WASHBUF A) 1:10 with ultrapure water.

Depending on how many replicates are to be run, dilute the urine sample 1:20 in 1× PBS in a 96-well plate. All proceeding steps will describe how to run this set of assays in duplicate with controls and standards also run in duplicate. Modifications to the plate plan and amount of sample can be made to run this in singlicate or triplicate.

Derivatization of standards, controls and samples is carried out in 2 mL deep 96-well plates, with one plate per assay.

Add 200 uL of standard (STD), 200 uL of control (CTRL), and 50 uL of diluted sample in the corresponding wells.

Add 150 uL of reaction buffer (DERBUF) only to the sample wells.

Add 50 uL derivatization reagent into the sample, STD, and CTRL wells.

Incubate for 1 hour at room temperature on a circular, horizontal shaker. This time may require modification. This is a chemical reaction step, as it is a chemical reaction that may come to completion faster in a hotter environment.

ADMA only: Add 250 uL dilution buffer (CODIL) into the sample, STD, and CTRL wells.

For SDMA, continue incubating during this period.

Incubate for 45 minutes at room temperature on a circular, horizontal shaker.

Assay Procedure

Take out the microtiter strips from the kit matching the number of CTRL/STD/sample wells needed for the ADMA and SDMA assays.

For ADMA and SDMA plates respectively: Take 2×50 uL from the sample, STD, and CTRL wells into the appropriate wells in the microtiter strips for duplicates.

Add 50 uL ADMA or SDMA antibody into each well for the ADMA or SDMA plate respectively.

Cover the microtiter plates tightly with foil and incubate overnight at 4° C.

Discard the content of each well and wash 5 times with 250 uL wash buffer on an automated plate washer.

Add 100 uL conjugate (CONJ) into each well.

Cover the microtiter plate tightly with foil and incubate for 1 hour at room temperature on a circular, horizontal shaker.

Discard the content of each well and wash 5 times with 250 uL wash buffer on an automated plate washer.

Add 100 uL substrate (SUB) into each well.

Incubate for 10-15 minutes at room temperature covered by a foil plate sealer.

Add 100 uL stop solution (STOP) into each well and mix on a plate shaker.

Determine absorption immediately with an ELISA reader at 450 nm and at 620 nm.

Standard Curve Generation and Interpolation

Using a 4-parameter logistic fit, create a curve correlating the concentration of the standards with the difference in absorption at 450 nm and 620 nm.

Interpolate sample unknown values to the curve. Although there is no sample concentration between 0 and 0.1 µM, the manufacturer sets the 0 value as 0.001 µM in generating the standard curve. This can be done if sample values are expected to fall below 0.1 µM.

Multiply the interpolated value by 20 to get the actual urine concentrations for SDMA and ADMA in the samples.

Expected Results

Figure 14:
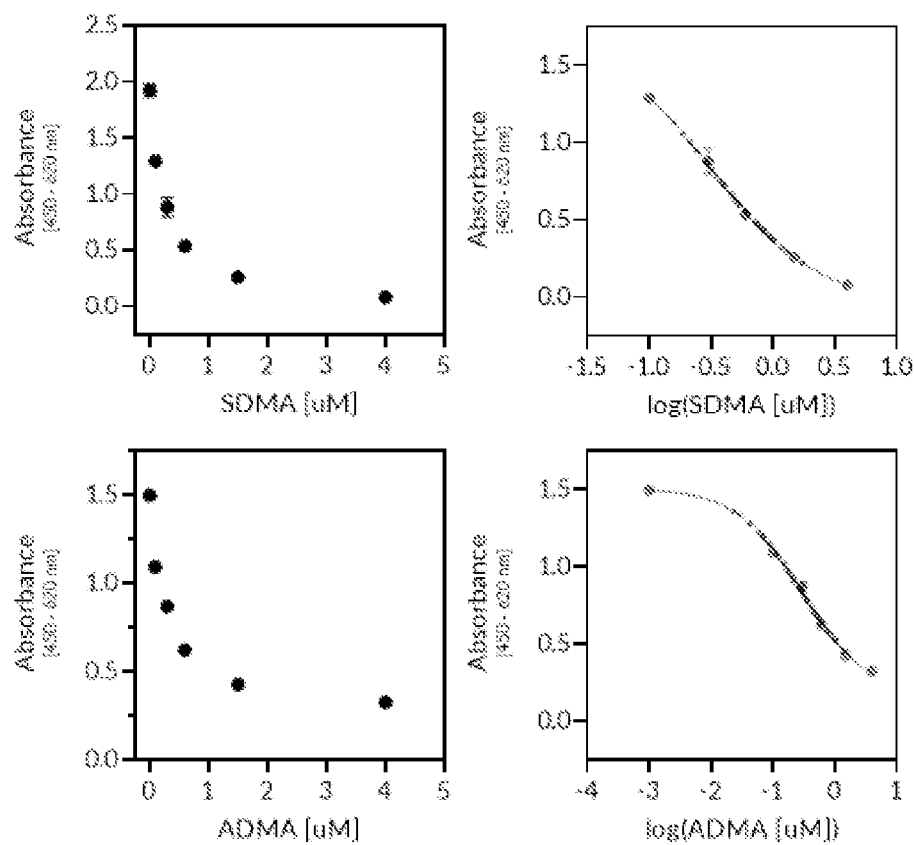
FIG. 14 illustrates results obtained for the detection of SDMA and ADMA in mammalian urine samples with the protocols described herein.

FIG. 14 illustrates expected results for the SDMA and ADMA assay. Squares indicate the interpolation of the urine samples. All urine samples were within the range of the assay.

The quantitative numbers detected by this assay can be inputted into one or more of the algorithms described above and the kidney function of the subject can be estimated.

Example 13

On 346 unique urine samples from 346 human patients, the $KIT_{Function}$/eGFR score was determined by measuring ADMA and using the equation:

KIT_GFR=141.922734943398+ 44.1991850006697*ADMA/Creatinine−max(Age, min (150.839900231942+−200.429015237454*ADMA/Creatinine−ADMA, Age*Protein−1403.95919636272− Creatinine*ADMA)). Detection of six biomarkers (CXCL10, cfDNA, m-cfDNA, creatinine, total protein, clusterin) had previously been measured on the same urine samples as described by PCT/US2017/047372. This $KIT_{Function}$/eGFR score was inputted into the KIT Score algorithm, thus providing a substitute for other blood-based eGFR tests described in the art.

Figure 15:
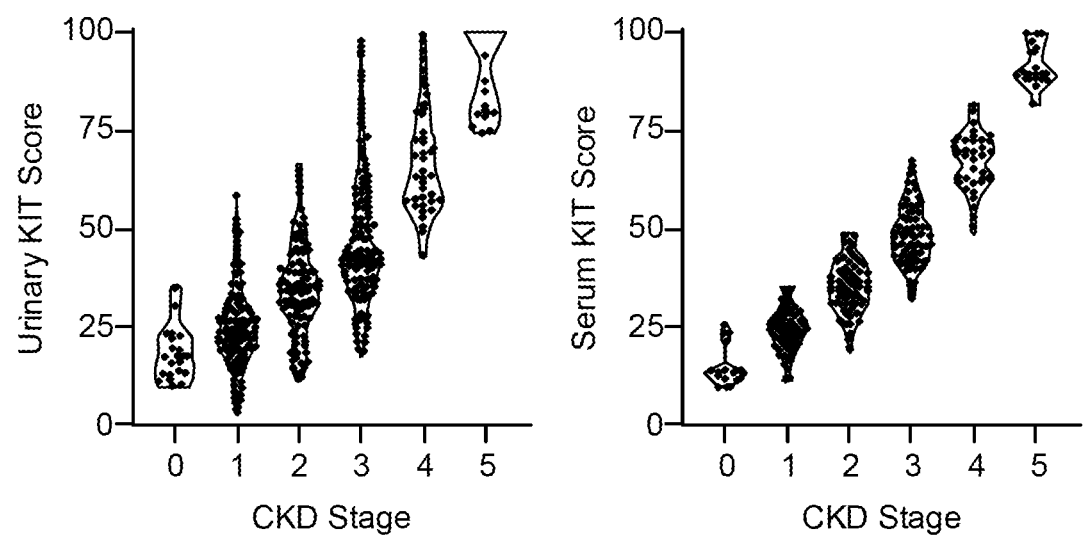
FIG. 15 illustrates a comparison of the performance of the method described herein in urine sample versus serum samples in five different stages of chronic kidney disease.

FIG. 15 illustrates a comparison of the performance of the method described herein in urine sample versus serum samples in five different stages of chronic kidney disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

What is claimed is:

1. A method for determining kidney function of a subject from a urine sample, the method comprising:
   detecting an amount of asymmetric dimethylarginine (ADMA) from a urine sample of a subject;
   assaying the urine sample to determine a hydration status of the subject; and
   generating a value indicative of the kidney function of the subject based on the amount of ADMA from the urine sample and the hydration status of the subject;
   determining the kidney function of the subject based on the value.

2. The method of claim 1, wherein generating a value indicative of the kidney function of the subject comprises inputting the amount of ADMA and the hydration status of the subject into an algorithm to produce the value.

3. The method of claim 2, wherein the algorithm is implemented via a computer system.

4. The method of claim 3, wherein determining the kidney function of the subject comprises comparing the value to a threshold and determining the kidney function of the subject based on the comparison.

5. The method of claim 4, wherein generating the value indicative of the kidney function of the subject comprises inputting a determined amount of a hydration marker from the urine sample into the algorithm to produce the value.

6. The method of claim 5, wherein the hydration marker is creatinine.

7. The method of claim 5, wherein the hydration marker is SDMA.

8. The method of claim 4, wherein generating the value indicative of the kidney function of the subject comprises inputting a density or specific gravity of the urine sample into the algorithm to produce the value.

9. The method of claim 2, wherein generating the value indicative of the kidney function of the subject comprises inputting an amount of total protein from the sample into the algorithm.

10. The method of claim 2, wherein generating the value indicative of the kidney function of the subject comprises inputting an age of the subject into the algorithm.

11. The method of claim 2, wherein generating the value indicative of the kidney function of the subject comprises inputting a gender of the subject into the algorithm.

12. The method of claim 2, wherein a race of the subject is not input into the algorithm.

13. The method of claim 1, wherein the amount of urine ADMA from the urine sample of the subject positively correlates with glomerular filtration rate (GFR).

14. The method of claim 1, wherein the value indicative of the kidney function of the subject is an estimated GFR.

15. The method of claim 1, wherein the hydration status of the subject is an amount of a urinary marker that is indicative of a hydration level in the subject.

16. The method of claim 15, wherein the urinary marker that is indicative of a hydration level in the subject is selected from the group consisting of urine SDMA or urine creatinine.

17. The method of claim 16, wherein assaying the urine sample to determine the hydration status of the subject comprises determining a density of the urine sample.

18. The method of claim 17, wherein the hydration status of the subject is represented by a specific gravity of the urine sample.

19. The method of claim 1, further comprising coupling a reagent to ADMA prior to detecting the amount of ADMA from the urine sample.

20. The method of claim 19, wherein the reagent is selected from N-hydrosuccinimido carbonic acid; (2,5-dioxopyrrolidin-1 yl) hydrogen carbonate (also known as succinimidocarbonate); N,N'-disuccinimidyl carbonate; carbonic acid (choloromethyl ester) (N-hydroxysuccinimide ester); or (2,5-dioxopyrrolidin-1-yl) prop-2-enyl carbonate.

21. The method of claim 20, wherein the step of detecting the amount of ADMA from the urine sample of the subject comprises:
   contacting the urine sample with an antibody that specifically binds to ADMA; and
   detecting an amount of the antibody that is in a bound state.

22. The method of claim 21, wherein the antibody that specifically binds ADMA has a reactivity for symmetric dimethylarginine (SDMA) that is less than 25%, less than 10%, less than 5%, or less than 1% of its reactivity for ADMA.

23. The method of claim 1, wherein the subject is identified as having impaired kidney function when the ADMA is in the urine sample at a concentration of less than 19.4 µM.

24. The method of claim 1, wherein the subject is identified as having impaired kidney function when an ADMA/creatinine ratio or ADMA/SDMA ratio is less than 0.3 µM/mg/dL or 0.7 µ/mg/dL, respectively.

25. The method of claim 1, further comprising (1) identifying the subject as having impaired kidney function and (2) administering a treatment to the subject based on the identified impairment of kidney function.

26. A method of detecting an amount of asymmetric dimethylarginine (ADMA) from a urine sample of a subject, the method comprising:
   a. obtaining a urine sample from the subject; and
   b. contacting the urine sample with an antibody that specifically binds to ADMA and
   detecting binding between the antibody and ADMA, wherein the subject is identified as having impaired kidney function when the ADMA is in the urine sample at a concentration of less than 19.4 µM.

27. A method of treating a disease or disorder associated with decreased kidney function or kidney disease in a subject, the method comprising:
   i) selecting a subject with having an ADMA concentration of less than 19.421 µM; or
   ii) selecting a subject having an ADMA/creatinine ratio less than 0.3 µM/mg/dL; or
   iii) selecting a subject having an ADMA/SDMA ratio less than 0.7 µM/mg/dL; and
   iv) treating the subject by administering a diabetic kidney disease-targeted drug, a SGLT-2 receptor inhibitor, a SIRT 1 agonist, a bromodomain inhibitor, a steroid, or dialysis to the subject.

* * * * *